United States Patent
Simkova et al.

(10) Patent No.: US 12,371,416 B2
(45) Date of Patent: Jul. 29, 2025

(54) COMPOUNDS FOR INHIBITION OF FIBROBLAST ACTIVATION PROTEIN

(71) Applicant: USTAV ORGANICKE CHEMIE A BIOCHEMIE AV CR, V. V. I., Prague (CZ)

(72) Inventors: Adela Simkova, Prague (CZ); Pavel Sacha, Prague (CZ); Natan Sidej, Prague (CZ); Tereza Ormsby, Prague (CZ); Jan Konvalinka, Prague (CZ)

(73) Assignee: USTAV ORGANICKE CHEMIE A BIOCHEMIE AV CR, V.V.I., Prague (CZ)

(*) Notice: Subject to any disclaimer, the term of this patent is extended or adjusted under 35 U.S.C. 154(b) by 481 days.

(21) Appl. No.: 17/913,128

(22) PCT Filed: Mar. 29, 2021

(86) PCT No.: PCT/CZ2021/050036
§ 371 (c)(1),
(2) Date: Sep. 20, 2022

(87) PCT Pub. No.: WO2021/197519
PCT Pub. Date: Oct. 7, 2021

(65) Prior Publication Data
US 2023/0192647 A1    Jun. 22, 2023

(30) Foreign Application Priority Data
Mar. 30, 2020  (CZ) ................ CZ2020-177

(51) Int. Cl.
C07D 401/12   (2006.01)
A61P 35/00    (2006.01)
C07D 401/14   (2006.01)

(52) U.S. Cl.
CPC ........... *C07D 401/12* (2013.01); *A61P 35/00* (2018.01); *C07D 401/14* (2013.01)

(58) Field of Classification Search
CPC ...... C07D 401/12; C07D 401/14; A61P 35/00
See application file for complete search history.

(56) References Cited

U.S. PATENT DOCUMENTS 5,965,556 A * 10/1999 Takeuchi ............. C07D 405/10
514/233.5

FOREIGN PATENT DOCUMENTS

WO    2013107820 A1    7/2013

OTHER PUBLICATIONS

Koen Jansen et al: Extended Structure-Activity Relationship and Pharmacokinetic Investigation of (4-Quinolinoyl) glycyl-2-cyanopyrrolidine Inhibitors of Fibroblast Activation Protein (FAP)11 , Journal of Medicinal Chemistry, vol. 57, No. 7, Mar. 11, 2014 (Mar. 11, 2014), pp. 3053-3074, XP055727968, http://dx.doi.org/10.1021/jm500031w , retrieved Sep. 20, 2022.
International Search Report and Written Opinion for corresponding PCT application No. PCT/CZ2021/050036, mailed Jun. 24, 2021.

* cited by examiner

*Primary Examiner* — Jeffrey S Lundgren
*Assistant Examiner* — W. Justin Youngblood
(74) *Attorney, Agent, or Firm* — Notaro, Michalos & Zaccaria P.C.

(57) ABSTRACT

Quinolinecarboxamide compounds of general formula I exceed the previously known FAP inhibitors in affinity and inhibitory effect. These agents can be used to specifically target tumours for diagnostic and therapeutic purposes, or for laboratory purposes in the study of endogenous FAP expression.

12 Claims, No Drawings

COMPOUNDS FOR INHIBITION OF FIBROBLAST ACTIVATION PROTEIN

FIELD OF ART

The aim of the invention is to provide new compounds that are suitable for targeting cancer therapy and diagnostics.

BACKGROUND ART

Fibroblast activation protein (FAP) is a serine protease expressed in many rapidly proliferating tissues, especially in the fibroblasts of epithelial tumours. Due to low or undetectable expression in healthy adult tissues, FAP is a promising platform for targeting cancer therapy and diagnosis. Although FAP has been implicated in tumour proliferation in many studies, the inhibition of FAP has not been shown to slow tumour growth (summarized in Busek et al. 2018, *Front. Biosci.*, 1933).

Due to its specific occurrence in pathological tissues and its anchorage on the outside of the plasma membrane of activated fibroblasts, FAP seems to be an ideal molecular address, thanks to which it is possible to precisely target tumour tissue. Initial studies have shown that this approach is relevant for the diagnosis of tumours using PET/CT. Conjugates of a selective FAP inhibitor with the DOTA chelator carrying the $^{68}$Ga radioactive isotope enabled a tumour tissue imaging sensitivity that is comparable to the currently used (18F)-fluorodeoxyglucose (FDG). A major advantage of this approach over the current method is the elimination of false positive signals generated by tissues with high glucose consumption (Lindner et al. 2018, *J. Nucl. Med.*, 1415).

Although the use of FAP molecular recognition as a platform for tumour targeting has been shown to be relevant, the natural expression of this enzyme in target tissues is still very low, and therefore the use of highly selective inhibitors or substrates with extremely high affinity is necessary. Due to the low concentrations of endogenously expressed FAP, this enzyme is also difficult to study under laboratory conditions, therefore models with the overexpression of FAP are used almost exclusively. Compounds of formula A and B (see below), which have the best affinity and selectivity properties to date (Jansen et al. 2014, *J. Med. Chem.*, 3053), are currently used to target FAP. The compound of formula B is the result of extensive research on the structure-activity relationship of FAP inhibitors, during which each part of its structure was highly optimized (e.g., Jansen et al. 2013, *ACS Med. Chem. Lett.*, 491; Poplawski et al. 2013, *J. Med. Chem.*, 3467; Ryabtsova et al. 2012, *Bioorg. Med. Chem. Lett.*, 3412). The molecule is derived from the FAP peptide substrate X-Gly-Pro-Y (wherein X and Y are arbitrary peptide sequences). The Gly-Pro motif is essential for the affinity of the substance for the FAP active site (Edosada et al. 2006, *FEBS Lett.*, 1581). The N-terminal 4 carbonylquinoline is the result of extensive optimization, and represents the most suitable substituent of said dipeptide Gly-Pro. For the purposes of inhibition, the peptide bond behind the proline in the FAP enzyme substrate can be replaced with an active head, i.e. a group that will have an electrophilic centre and will be capable of undergoing nucleophilic attack at the catalytic site of the enzyme.

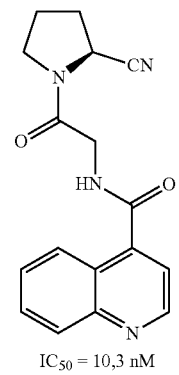

A $IC_{50} = 10{,}3$ nM

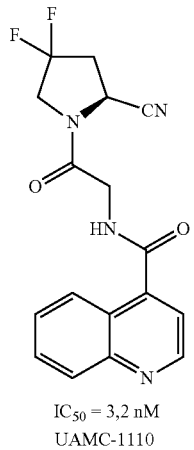

B $IC_{50} = 3{,}2$ nM

UAMC-1110

So far, only the following functional groups have been used for this purpose: boronic acid, chloromethyl ketone and nitrile. It is the nitrile group that has worked the most so far, and nitrile FAP inhibitors have been used to target tumours in vivo (Lindner et al. 2018, *J. Nucl. Med.*, 1415).

As was mentioned above, extreme affinity of the inhibitor is necessary for the optimal targeting of FAP in vivo and in vitro. Although the N-terminal portion of the inhibitor molecule has been highly optimized, the C-terminal portion has not yet been explored. Thus optimizing this part of the molecule also opens up the possibility of further increasing the desired affinity of the inhibitor.

In this invention, we show that by using a substitutable active head, specifically α-ketoamide, it is possible to unexpectedly expand the number of interactions of the inhibitor with the active site of the enzyme and thus significantly improve the affinity of this inhibitor for FAP.

From an extensive study of the relationship between structure and activity, we have obtained a number of substances which far exceed all previously known FAP inhibitors in terms of their affinity and ability to inhibit. These substances can be used for analogous applications that have already been mentioned, i.e. for the specific targeting of tumours for diagnostic and therapeutic purposes, or for laboratory purposes in the study of endogenous FAP expression.

DISCLOSURE OF THE INVENTION

The present invention is based on the use of a novel active head, specifically α-ketoamide, to form a novel and unexpectedly highly effective compound for inhibiting fibroblast activation protein (FAP). The nitrogen substitutions proposed here for the α-ketoamide group dramatically increase the affinity of the substances for FAP. The disclosed compounds can be used to target tumour tissues for diagnostic or therapeutic purposes.

The present invention provides quinolinecarboxamide compounds exhibiting high inhibitory activity against fibroblast activation protein (FAP), said compounds having the general formula I

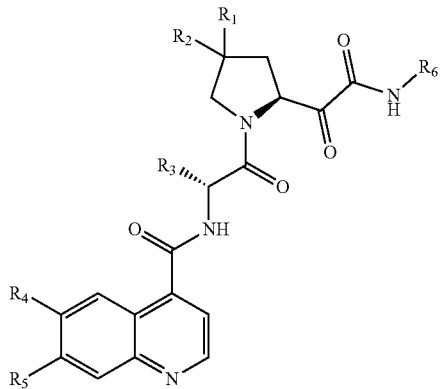

wherein $R_1$ and $R_2$ are independently selected from the group consisting of H, D, and F, $R_3$ is selected from the group consisting of H, D, and C1-C5 alkyl, $R_4$ and $R_5$ are independently selected from the group consisting of H, D, —OH, C1-C3 alkoxy and the structure —X—Y—Z, wherein X is oxygen or —NH—, Y is

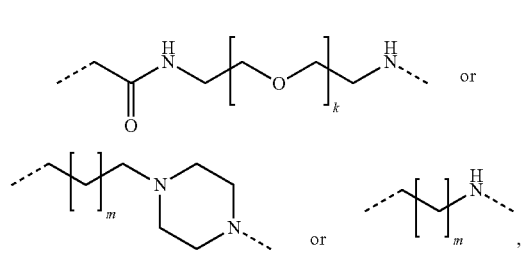

wherein k is an integer from 5 to 15 and m is an integer from 1 to 3, and Z is

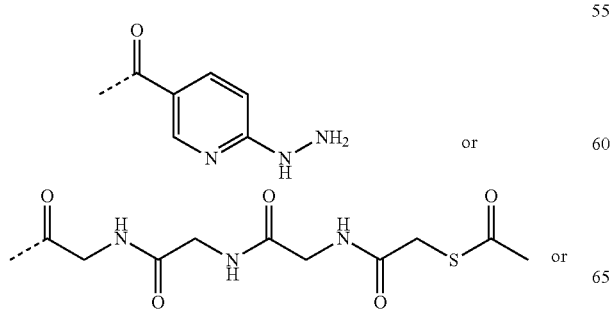

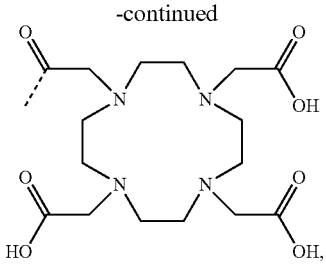

$R_6$ is selected from the group consisting of H, D, C1-C10 alkyl, C3-C10 cycloalkyl, adamantyl, and substituted or unsubstituted aryl or C7-C20 alkylaryl, wherein the aryl is

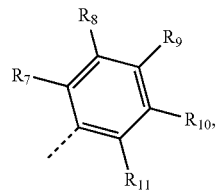

wherein $R_7$ and $R_{11}$ are independently selected from the group consisting of H, D, halogen, C1-C3 alkyl, C1-C3 alkoxy, —$CF_3$, and —C(=O)—$OR_{12}$, wherein $R_{12}$ is selected from the group consisting of H, D, halogen, C1-C4 alkyl, and C1-C2 alkyl, $R_8$, $R_9$ and $R_{10}$ are independently selected from the group consisting of H, D, halogen, —OMe, C1-C3 alkyl, C1-C3 alkoxy or C1-C2 alkoxy, —$CF_3$, and —C(=O)—$OR_{12}$, or $R_6$ is

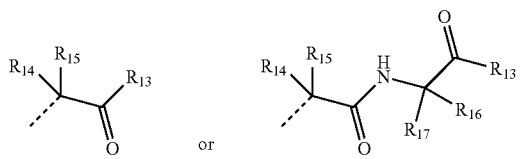

wherein $R_{13}$ is selected from the group consisting of —$OR_{12}$, —$NHR_{12}$, —N(—$CH_3$)$R_{12}$, pyrrolidine, and morpholine, $R_{14}$ and $R_{15}$ are independently selected from the group consisting of H, D, C1-C5 alkyl, phenyl, 3,4-dimethoxyphenyl, benzyl, 3,4-dimethoxybenzyl, and unsubstituted C3-C8 heteroalkylaryl, $R_{16}$ and $R_{17}$ are independently selected from the group consisting of H, D, C1-C6 alkyl, phenyl, benzyl, 4-hydroxybenzyl, unsubstituted C3-C8 heteroalkylaryl, —$(CH_2)_n$—C(=O)—$OR_{18}$, —$(CH_2)_n$—C(=O)—$NR_{19}R_{20}$, and —$(CH_2)_n$—$NR_{21}R_{22}$, wherein n is an integer from 1 to 4, $R_{18}$ is selected from the group consisting of H, D, C1-C3 alkyl, and benzyl, $R_{19}$ and $R_{20}$ are independently selected from the group consisting of H, D, C1-C3 alkyl, benzyl, and 3,4-dimethoxybenzyl, and $R_{21}$ and $R_{22}$ are independently selected from the group consisting of H, D, and (benzyloxy)carbonyl.

As described herein, and unless otherwise indicated, individual substituents have the following meanings:

alkyl is a straight or branched hydrocarbon chain containing the number of carbons indicated at each occurrence of this term and specifically includes methyl, ethyl, propyl, isopropyl, butyl, isobutyl, s-butyl, t-butyl, pentyl, isopentyl, neopentyl, hexyl, isohexyl, cyclohexyl, cyclohexylmethyl, 3-methylpentyl, 2,2-dimethylbutyl, 2,3-dimethylbutyl and the like;

cycloalkyl is a cyclic hydrocarbon chain containing the number of carbons indicated at each occurrence of this term and specifically includes cyclopropyl, cyclopentyl, cyclohexyl, and the like;

heterocycloalkyl is a cyclic hydrocarbon chain containing the number of carbons indicated at each occurrence of this term and containing at least one nitrogen or oxygen atom, and specifically includes pyrrolidine, piperidine, tetrahydrofuran, tetrahydropyran, piperazine, morpholine, aryl is a hydrocarbon group containing one or more aromatic nuclei, containing the number of carbons indicated at each occurrence of this term, and may be unsubstituted or substituted with one or more substituents selected from the group consisting of D, —OH, alkoxy, $NH_2$, $—NO_2$, —CN, —C(=O)—O-alkyl and halogen, heteroalkylaryl is an alkyl group bearing at least one aromatic nucleus containing the number of carbons indicated at each occurrence of this term and at least one heteroatom from the group consisting of oxygen, nitrogen and sulfur, preferably aryl is selected from pyrrole, furan, thiophene, imidazole, thiazole, oxazole, indole and pyridine, and may be unsubstituted or substituted with one or more substituents selected from the group consisting of —OH, —O(aryl), —O(arylalkyl), —C(O)—, —CN, and halogen;

alkylaryl denotes an alkyl group which is substituted with one or more aryl groups unsubstituted or substituted with one or more of the substituents selected from the group consisting of D, —OH, alkyl, alkoxy, —O(aryl), —O(arylalkyl), —C(=O)—, —C(=O)—O-alkyl, —CN, and halogen;

alkoxy means a saturated, straight or branched, C1 to C10 hydrocarbon chain directly attached through an oxygen atom, and specifically includes methoxy, ethoxy, propoxy, isopropoxy, butoxy, isobutoxy, t-butoxy, pentyloxy, isopentyloxy, neopentyloxy, hexyloxy, isohexyloxy, and the like.

The invention further provides compounds of general formula I, selected from the group consisting of (S)—N-(2-(2-(2-(Benzylamino)-2-oxoacetyl)pyrrolidin-1-yl)-2-oxoethyl)quinoline-4-carboxamide, (S)—N-(2-(2-(2-((3,4-Dimethoxybenzyl)amino)-2-oxoacetyl)pyrrolidin-1-yl)-2-oxoethyl)-quinoline-4-carboxamide, (S)—N-(2-(2-(2-((4-Fluorobenzyl)amino)-2-oxoacetyl)pyrrolidin-1-yl)-2-oxoethyl)quinoline-4-carboxamide, (S)—N-(2-Oxo-2-(2-(2-oxo-2-(phenethylamino)acetyl)pyrrolidin-1-yl)ethyl)quinoline-4-carboxamide, (S)—N-(2-(2-(2-((3,4-Dimethoxyphenethyl)amino)-2-oxoacetyl)pyrrolidin-1-yl)-2-oxoethyl)quinoline-4-carboxamide, (S)—N-(2-(2-(2-((4-Methoxyphenyl)amino)-2-oxoacetyl)pyrrolidin-1-yl)-2-oxoethyl)quinoline-4-carboxamide, Methyl(S)-4-(2-oxo-2-(1-((quinoline-4-carbonyl)glycyl)pyrrolidin-2-yl)acetamido)benzoate, (S)—N-(2-(2-(2-(Cyclopropylamino)-2-oxoacetyl)pyrrolidin-1-yl)-2-oxoethyl)quinoline-4-carboxamide, (S)—N-(2-(2-(2-(Isopropylamino)-2-oxoacetyl)pyrrolidin-1-yl)-2-oxoethyl)quinoline-4-carboxamide, (S)—N-(2-Oxo-2-(2-(2-oxo-2-(pentylamino)acetyl)pyrrolidin-1-yl)ethyl)quinoline-4-carboxamide, Methyl (S)-(2-oxo-2-(1-((quinoline-4-carbonyl)glycyl)pyrrolidin-2-yl)acetyl)glycinate, tert-Butyl (S)-(2-oxo-2-(1-((quinoline-4-carbonyl)glycyl)pyrrolidin-2-yl)acetyl)glycinate, Methyl (2-oxo-2-((S)-1-((quinoline-4-carbonyl)glycyl)pyrrolidin-2-yl)acetyl)alaninate, (S)—N-(2-(2-(2-((2-(Dimethylamino)-2-oxoethyl)amino)-2-oxoacetyl)pyrrolidin-1-yl)-2-oxoethyl)quinoline-4-carboxamide, (S)—N-(2-(2-(2-((2-(Ethyl(propyl)amino)-2-oxoethyl)amino)-2-oxoacetyl)pyrrolidin-1-yl)-2-oxoethyl)quinoline-4-carboxamide, (S)—N-(2-(2-(2-((2-(Isopropylamino)-2-oxoethyl)amino)-2-oxoacetyl)pyrrolidin-1-yl)-2-oxoethyl)quinoline-4-carboxamide, (S)—N-(2-(2-(2-((2-(Benzylamino)-2-oxoethyl)amino)-2-oxoacetyl)pyrrolidin-1-yl)-2-oxoethyl)quinoline-4-carboxamide, Methyl (2-oxo-2-((S)-1-((quinoline-4-carbonyl)glycyl)pyrrolidin-2-yl)acetyl)glycyl-L-leucinate, Methyl (2-oxo-2-((S)-1-((quinoline-4-carbonyl)glycyl)pyrrolidin-2-yl)acetyl)glycyl-L-phenylalaninate, Methyl (2-oxo-2-((S)-1-((quinoline-4-carbonyl)glycyl)pyrrolidin-2-yl)acetyl)glycyl-L-glutaminate, 5-Benzyl 1-methyl (2-oxo-2-((S)-1-((quinoline-4-carbonyl)glycyl)pyrrolidin-2-yl)acetyl)-glycyl-L-glutamate, Benzyl $N^6$-((benzyloxy)carbonyl)-$N^2$-((2-oxo-2-((S)-1-((quinoline-4-carbonyl)glycyl)-pyrrolidin-2-yl)acetyl)glycyl)-L-lysinate, (S)—S-(62-((4-((2-(2-(2-((3,4-dimethoxybenzyl)amino)-2-oxoacetyl)pyrrolidin-1-yl)-2-oxoethyl)carbamoyl)quinoline-7-yl)oxy)-2,5,8,11,61-pentaoxo-15,18,21,24,27,30,33,36,39,42,45,48,51,54,57-pentadecaoxa-3,6,9,12,60-pentaaza-dohexacontyl)-ethanethioate, and (S)—N-(2-(2-(2-((3,4-dimethoxybenzyl)amino)-2-oxoacetyl)pyrrolidin-1-yl)-2-oxoethyl)-7-(2-(6-hydrazinylnicotinamido)ethoxy)quinoline-4-carboxamide.

The invention furthermore relates to compounds of general formula I for use as medicaments.

The invention further relates to compounds of general formula I for use as medicaments in the treatment of cancer.

The invention further relates to compounds of general formula I for use as medicaments in the treatment of epithelial tumours.

The invention also relates to compounds of general formula I for use in targeted diagnostics of tumour tissue, in particular epithelial tumours.

The invention further provides a pharmaceutical composition comprising a therapeutically effective amount of the compound of general formula I and optionally at least one pharmaceutically acceptable carrier, filler and/or diluent.

The invention also relates to a pharmaceutical composition comprising a therapeutically effective amount of the compound of general formula I optionally at least one pharmaceutically acceptable carrier, filler and/or diluent, for use in the treatment of cancer, in particular of epithelial tumours.

The invention also relates to a diagnostic composition comprising the compound of general formula I and optionally at least one pharmaceutically acceptable carrier, filler and/or diluent.

The invention also relates to a diagnostic composition comprising the compound of general formula I and optionally at least one pharmaceutically acceptable carrier, filler and/or diluent for use in targeted diagnostics of tumour tissue, in particular of epithelial tumours.

To verify the applicability of the compounds in in vivo applications, i.e. both for the pharmaceutical inhibition of the FAP enzyme and for the use of conjugates of the compounds for diagnostic and therapeutic purposes, selectivity to related proteins, stability in murine and human plasma, stability in murine microsomes and cytotoxicity on human tumour lines has been measured for selected compounds. The $IC_{50}$ (mean inhibitory concentration) of the selected compounds was measured using the enzymes dipeptidyl peptidase IV and prolyl endopeptidase (DPPIV and PREP), to determine possible interferences of the compounds with these enzymes. It was confirmed that there is no risk of interference with DPPIV due to the high $IC_{50}$ value; hence the substances bind significantly less to the enzyme than to FAP. Although these compounds bind to PREP as well as to FAP, PREP is present mainly in the cytosol, so the interference is insignificant—the compounds do not come into contact with this enzyme in vivo.

The best tested compound is more than 20 times more potent than the previously mentioned substance "B" (i.e. UAMC-1110), which is generally considered to be the best compound known in the state of the art. However, even more relevant is the comparison with substance "A" (without two fluorine atoms), the composition of which is most similar to the compounds of the present invention. The most potent of them are more than two orders of magnitude more sensitive to FAP (150 times).

The most potent compound 3b exhibits an excellent stability in both plasma and microsomes. It is therefore suitable for in vivo applications targeting the FAP enzyme. Importantly, due to its high stability in murine plasma and microsomes, it will be possible to use mouse models during the development of these applications.

In general, the low cytotoxicity of the compounds of the invention (including the most potent compound 3b) measured at two concentrations (differing by 1 order of magnitude) in four human tumour cell lines is crucial for the possible future use of the compounds of this type for in vivo applications.

Said compounds can be synthesized according to Schemes 1-4 from Boc-L-prolinal, Cbz-glycine and the corresponding isonitrile by the Passerini reaction. The resulting α-acyloxyamide is further acid deprotected and basic transacylated to give the corresponding α-hydroxyamide. This compound can be subjected to modifications through peptide-forming condensations and through gentle introduction and removal of protecting groups. The resulting α-hydroxyamide is then oxidized to the final α-ketoamide. For derivatives 12 and 15, the oxidation had to be performed before the introduction of hydrazinonicotinic acid (HYNIC) or mercaptoacetyltriglycine (MAG3) due to the incompatibility of these structures with the oxidation step.

The synthetic approach is illustrated in the following schemes:

Scheme 1

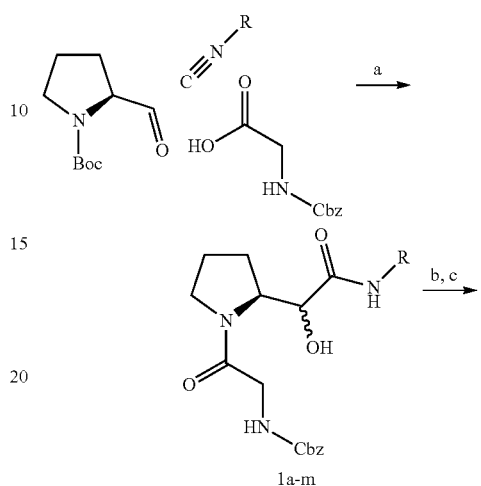

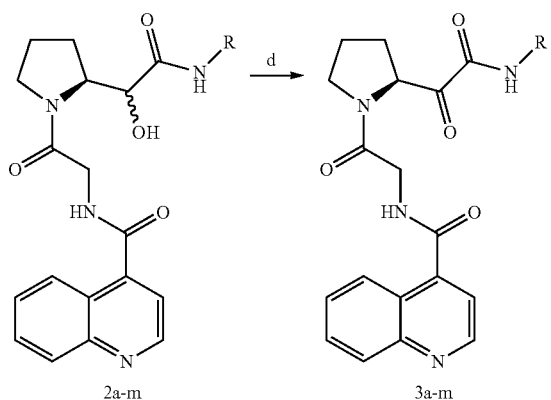

Scheme 2

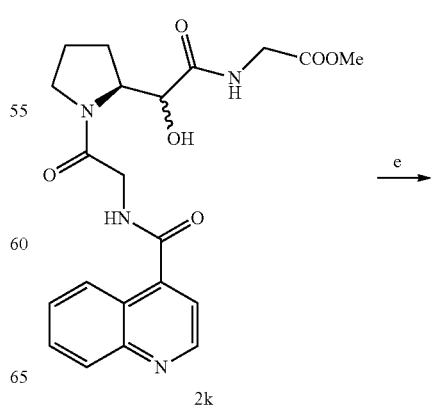

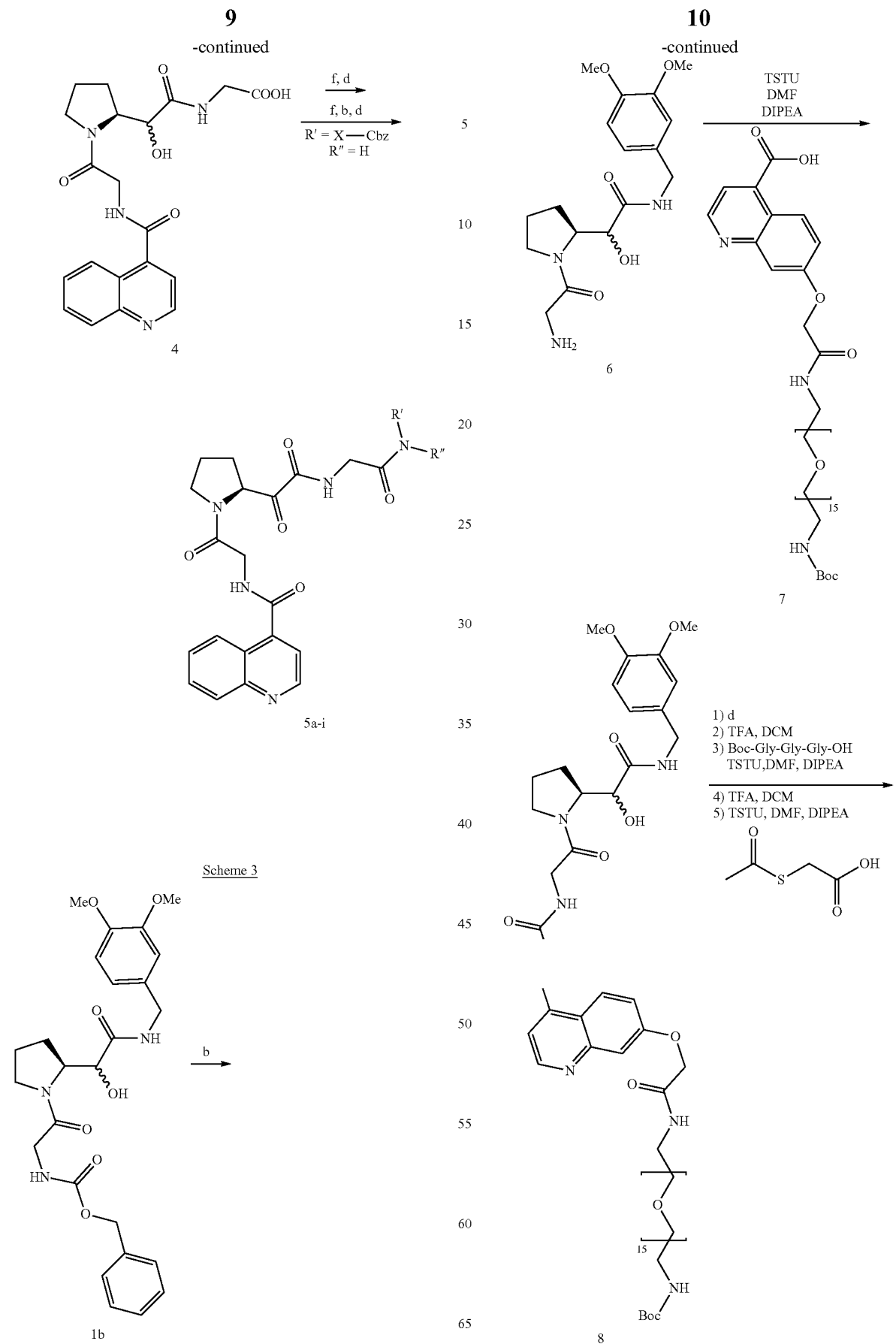

-continued
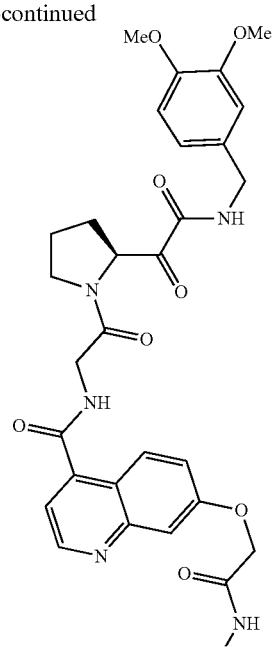
Scheme 4
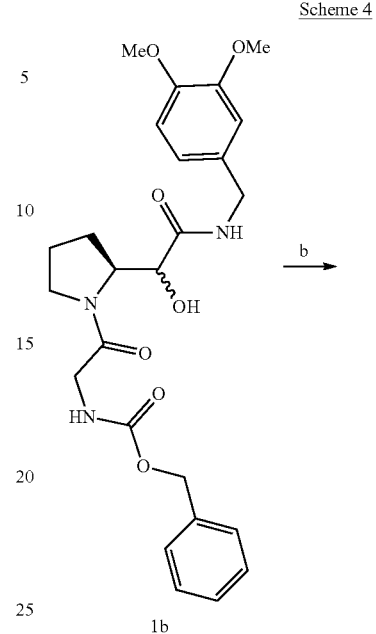
1b
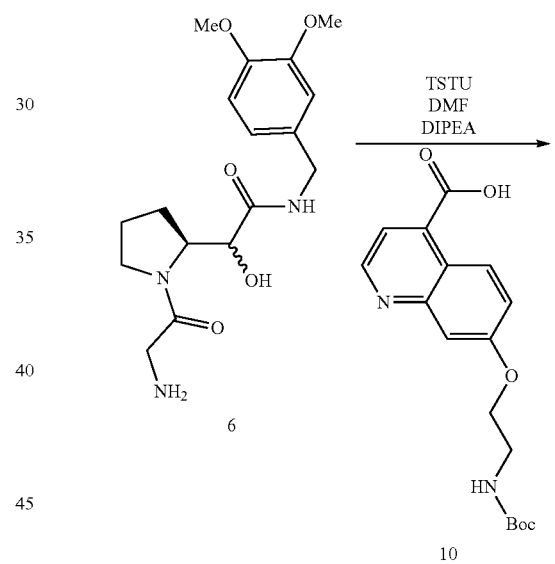
6
10
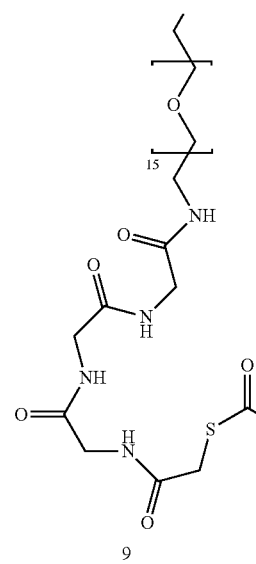
9
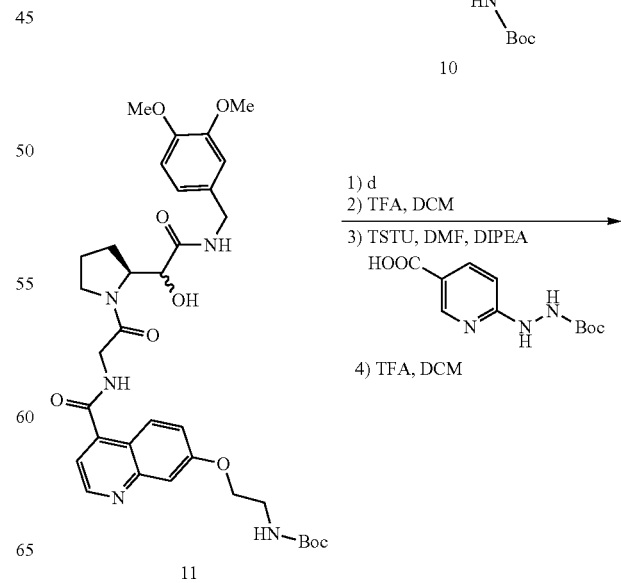
11
1) d
2) TFA, DCM
3) TSTU, DMF, DIPEA
4) TFA, DCM -continued

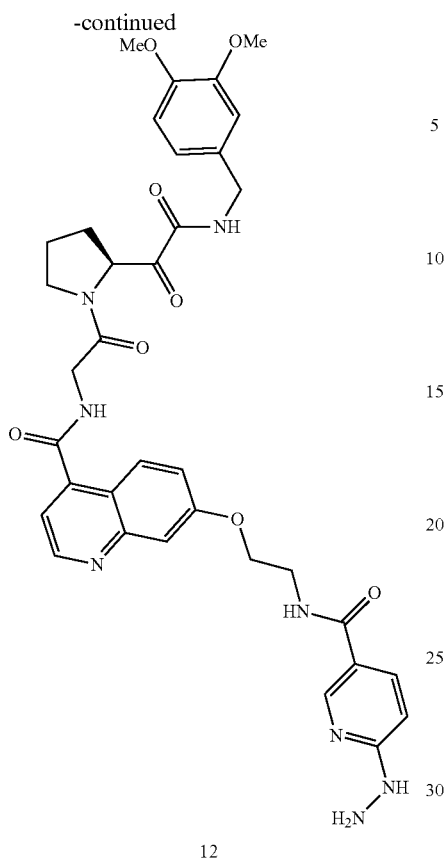

12

Reaction conditions valid for Schemes 1-4:
a: 1) DCM, rt, 2) DCM, TFA, rt, 3) DCM, Et₃N, rt, b: H₂, Pd(OH)₂/C, MeOH, rt, c: Quinoline-4-carboxylic acid, TSTU, DIPEA, DMF, rt, d: IBX, DMSO, rt, e: 1% KOH, 90% MeOH, f: 1) TSTU, DIPEA, DMF, 2) R'—NH—R", DMF; X=—CH(COOMe)(CH₂)₄NH—

EXAMPLES

List of Abbreviations bd broad dublet
Bn benzyl
Boc terc-butyloxycarbonyl
bt broad triplet
Cbz benzyloxycarbonyl
CCRF-CEM human lymphoblastoid leukemia tumour cell line
Cp cyclopropyl
CT computed tomography
d doublet
DCM dichloromethane
dd doublet of doublets
ddd doublet of doublets of doublets
DIPEA diisopropylethylamine
DMF dimethylformamide
DMSO dimethyl sulfoxide
DOTA 1,4,7,10-tetraazacyclododecane-1,4,7,10-tetraacetic acid
DPPIV dipeptidyl peptidase IV
ekv. molar equivalent
FAP fibroblast activation protein
FDG (18F)-fluorodeoxyglucose
Gly glycine
Hela human cervical carcinoma cell line
HepG2 human liver carcinoma cell line
HL-60 human myeloid leukemia cell line
HPLC high-performance liquid chromatography
HR MS high-resolution mass spectrum
HYNIC hydrazinonicotinic acid
IBX iodoxybenzoic acid
IC₅₀ mean inhibitory concentration
LC-MS tandem of liquid chromatography and mass spectrometry
m multiplet
MAG3 mercaptoacetyltriglycine
MeOH methanol
NMR nuclear magnetic resonance
PDA light detector with diode array
PET positron emission tomography
Ph phenyl
PREP prolyl endopeptidase
Pro proline
QDA mass detector with Dalton quadrupole
Rt retention time
s singlet
SPECT single-photon emission computed tomography
TFA trifluoroacetic acid
TSTU N,N,N',N'-Tetramethyl-O—(N-succinimidyl)uronium tetrafluoroborate
UHPLC-MS tandem of ultra-high performance liquid chromatography and mass spectrometry
UV ultraviolet rays
vol./vol. proportion of volume units
wt./wt. proportion of weight units Instruments Used in the Synthesis of Compounds Prepared in the Examples Below NMR spectra were measured in a Bruker Avance III 500 MHz spectrometer ($^1$H at 500 MHz and $^{13}$C at 125.7 MHz). High-resolution mass spectra (HR MS) were measured in an LTQ Orbitrap XL hybrid mass spectrometer (Thermo Fisher Scientific, Waltham, MA, USA) using electrospray ionization. During the synthesis, the substances were purified by reversed-phase FLASH chromatography (silica gel C18 230-400 mesh) in a Teledyne ISCO CombiFLASH Rf+with a dual UV detector (210 and 254 nm) using a gradient of 0.1% (vol./vol.) aqueous solution of trifluoroacetic acid→acetonitrile. Purity and conversion during the reactions were monitored by UHPLC-MS in a Waters Acquity H-class UPLC with PDA (diode array, 190-800 nm) and QDA (100-1250 m/z) detectors using a Bischoff ProntoSIL HPLC column (100×2.0 mm, Prontopearl TPP 120-2.2-C18 SH, 2.2 µm) and a gradient of water→acetonitrile with the addition of 0.1% (vol./vol.) formic acid at a flow rate of 0.5 ml/min.

Overview of the Compounds Prepared in the Examples Below

| Example | Compound | Structure | Systematic name |
|---|---|---|---|
| 1 | 3a | 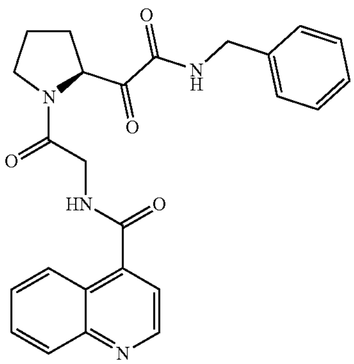 [SMILES: O=C(NCc1ccccc1)C(=O)[C@@H]1CCCN1C(=O)CNC(=O)c1ccnc2ccccc12] | (S)-N-(2-(2-(2-(Benzylamino)-2-oxoacetyl)pyrrolidin-1-yl)-2-oxoethyl)quinoline-4-carboxamide |
| 2 | 3b | 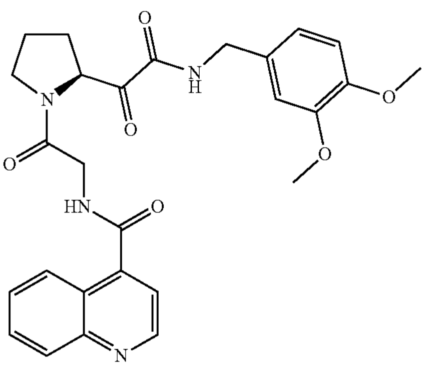 [SMILES: COc1ccc(CNC(=O)C(=O)[C@@H]2CCCN2C(=O)CNC(=O)c2ccnc3ccccc23)cc1OC] | (S)-N-(2-(2-(2-(3,4-Dimethoxybenzyl)amino)-2-oxoacetyl)pyrrolidin-1-yl)-2-oxoethyl)quinoline-4-carboxamide |
| 3 | 3c | 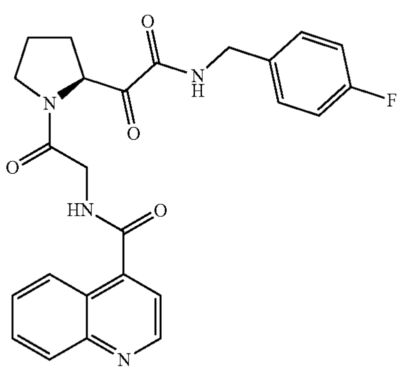 [SMILES: O=C(NCc1ccc(F)cc1)C(=O)[C@@H]1CCCN1C(=O)CNC(=O)c1ccnc2ccccc12] | (S)-N-(2-(2-(2-((4-Fluorobenzyl)amino)-2-oxoacetyl)pyrrolidin-1-yl)-2-oxoethyl)quinoline-4-carboxamide |
| 4 | 3d | 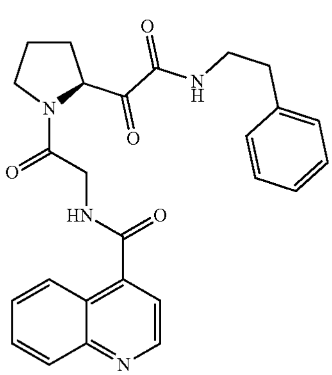 [SMILES: O=C(NCCc1ccccc1)C(=O)[C@@H]1CCCN1C(=O)CNC(=O)c1ccnc2ccccc12] | (S)-N-(2-Oxo-2-(2-(2-oxo-2-(phenethylamino)acetyl)pyrrolidin-1-yl)ethyl)quinoline-4-carboxamide |

-continued

| Example | Compound | Structure | Systematic name |
|---|---|---|---|
| 5 | 3e | 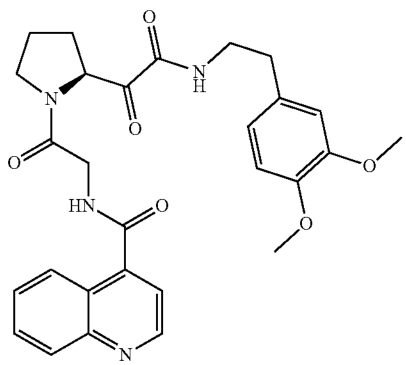 [SMILES: COc1ccc(CCNC(=O)C(=O)[C@@H]2CCCN2C(=O)CNC(=O)c2ccnc3ccccc23)cc1OC] | (S)-N-(2-(2-(2-((3,4-Dimethoxyphenethyl)amino)-2-oxoacetyl)pyrrolidin-1-yl)-2-oxoethyl)quinoline-4-carboxamide |
| 6 | 3f | 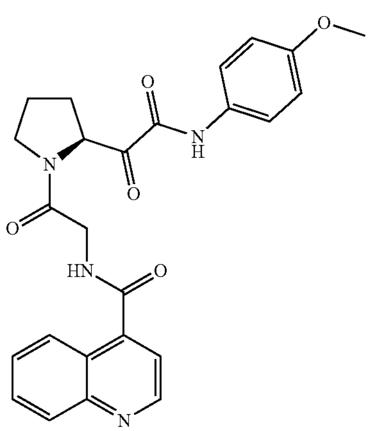 [SMILES: COc1ccc(NC(=O)C(=O)[C@@H]2CCCN2C(=O)CNC(=O)c2ccnc3ccccc23)cc1] | (S)-N-(2-(2-(2-((4-Methoxyphenyl)amino)-2-oxoacetyl)pyrrolidin-1-yl)-2-oxoethyl)quinoline-4-carboxamide |
| 7 | 3g | 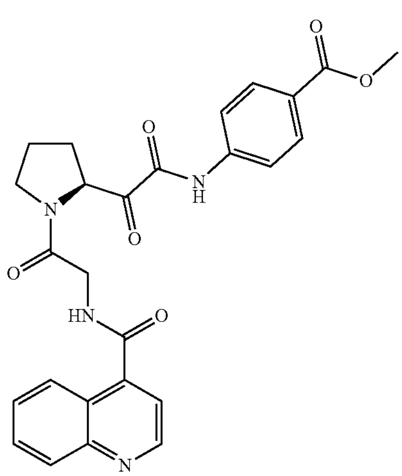 [SMILES: COC(=O)c1ccc(NC(=O)C(=O)[C@@H]2CCCN2C(=O)CNC(=O)c2ccnc3ccccc23)cc1] | Methyl(S)-4-(2-oxo-2-(1-((quinoline-4-carbonyl)glycyl)-pyrrolidin-2-yl)acetamido)-benzoate |

| Example | Compound | Structure | Systematic name |
|---|---|---|---|
| 8 | 3h | 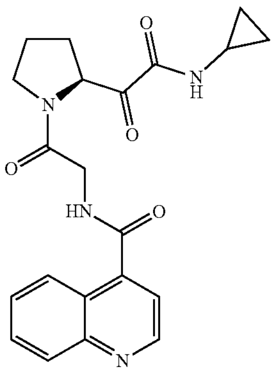 [SMILES: O=C(NC1CC1)C(=O)[C@@H]1CCCN1C(=O)CNC(=O)c1ccnc2ccccc12] | (S)-N-(2-(2-(2-(Cyclopropylamino)-2-oxoacetyl)pyrrolidin-1-yl)-2-oxoethyl)quinoline-4-carboxamide |
| 9 | 3i | 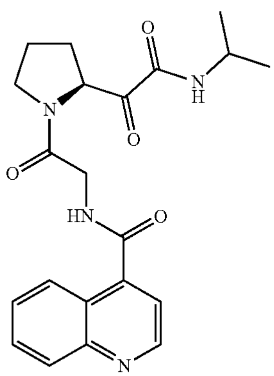 [SMILES: CC(C)NC(=O)C(=O)[C@@H]1CCCN1C(=O)CNC(=O)c1ccnc2ccccc12] | (S)-N-(2-(2-(2-(Isopropylamino)-2-oxoacetyl)pyrrolidin-1-yl)-2-oxoethyl)quinoline-4-carboxamide |
| 10 | 3j | 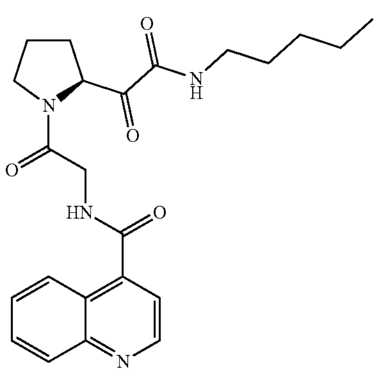 [SMILES: CCCCCNC(=O)C(=O)[C@@H]1CCCN1C(=O)CNC(=O)c1ccnc2ccccc12] | (S)-N-(2-Oxo-2-(2-(2-oxo-2-(pentylamino)acetyl)pyrrolidin-1-yl)ethyl)quinoline-4-carboxamide |
| 11 | 3k | 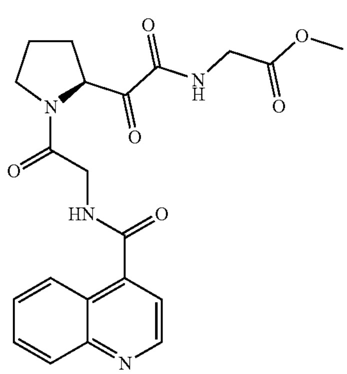 [SMILES: COC(=O)CNC(=O)C(=O)[C@@H]1CCCN1C(=O)CNC(=O)c1ccnc2ccccc12] | Methyl(S)-(2-oxo-2-(1-((quinoline-4-carbonyl)glycyl)pyrrolidin-2-yl)acetyl)glycinate |

-continued

| Example | Compound | Structure | Systematic name |
|---|---|---|---|
| 12 | 3l | 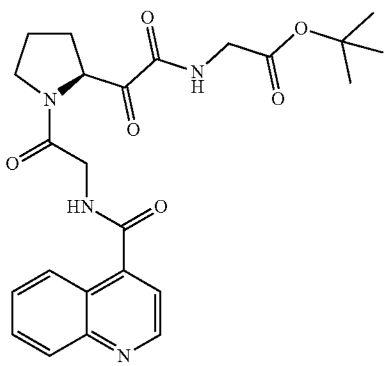 [SMILES: CC(C)(C)OC(=O)CNC(=O)C(=O)[C@@H]1CCCN1C(=O)CNC(=O)c1ccnc2ccccc12] | terc-Butyl(S)-(2-oxo-2-(1-((quinoline-4-carbonyl)glycyl)-pyrrolidin-2-yl)acetyl)glycinate |
| 13 | 3m | 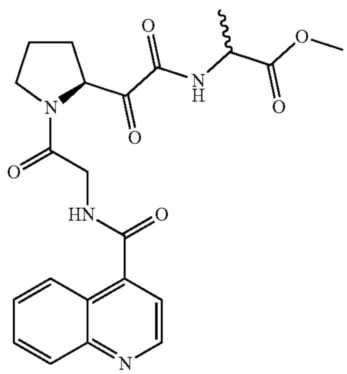 [SMILES: COC(=O)C(C)NC(=O)C(=O)[C@@H]1CCCN1C(=O)CNC(=O)c1ccnc2ccccc12] | Methyl(2-oxo-2-((S)-1-((quinoline-4-carbonyl)-glycyl)pyrrolidin-2-yl)acetyl)alaninate |
| 14 | 5a | 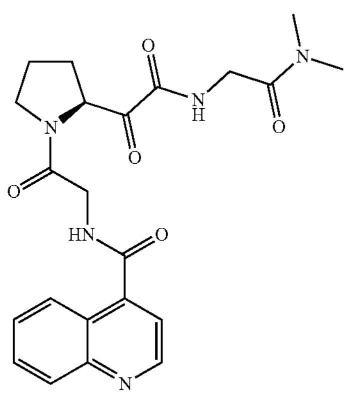 [SMILES: CN(C)C(=O)CNC(=O)C(=O)[C@@H]1CCCN1C(=O)CNC(=O)c1ccnc2ccccc12] | (S)-N-(2-(2-(2-((2-(Dimethylamino)-2-oxoethyl)amino)-2-oxoacetyl)pyrrolidin-1-yl)-2-oxoethyl)quinoline-4-carboxamide |
| 15 | 5b | 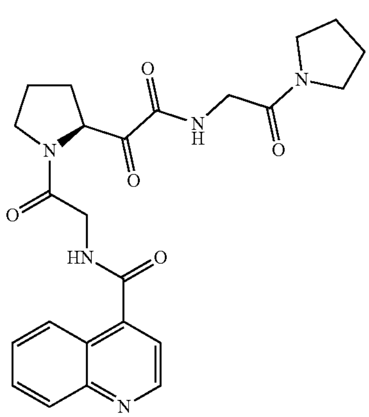 [SMILES: O=C(NCC(=O)N1CCCC1)C(=O)[C@@H]1CCCN1C(=O)CNC(=O)c1ccnc2ccccc12] | (S)-N-(2-(2-(2-((2-(Ethyl(propyl)amino)-2-oxoethyl)amino)-2-oxoacetyl)pyrrolidin-1-yl)-2-oxoethyl)quinoline-4-carboxamide |

-continued

| Example | Compound | Structure | Systematic name |
|---|---|---|---|
| 16 | 5c | 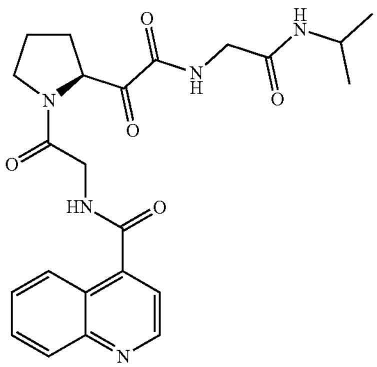 [SMILES: CC(C)NC(=O)CNC(=O)C(=O)[C@@H]1CCCN1C(=O)CNC(=O)c1ccnc2ccccc12] | (S)-N-(2-(2-(2-((2-(Isopropylamino)-2-oxoethyl)amino)-2-oxoacetyl)pyrrolidin-1-yl)-2-oxoethyl)quinoline-4-carboxamide |
| 17 | 5d | 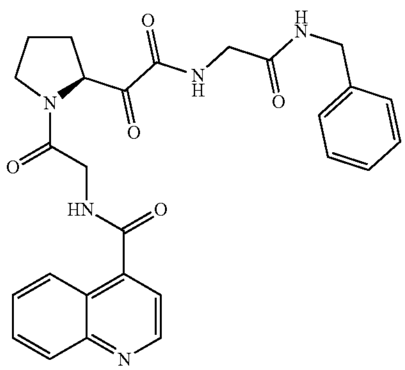 [SMILES: O=C(CNC(=O)C(=O)[C@@H]1CCCN1C(=O)CNC(=O)c1ccnc2ccccc12)NCc1ccccc1] | (S)-N-(2-(2-(2-((2-(Benzylamino)-2-oxoethyl)amino)-2-oxoacetyl)pyrrolidin-1-yl)-2-oxoethyl)quinoline-4-carboxamide |
| 18 | 5e | 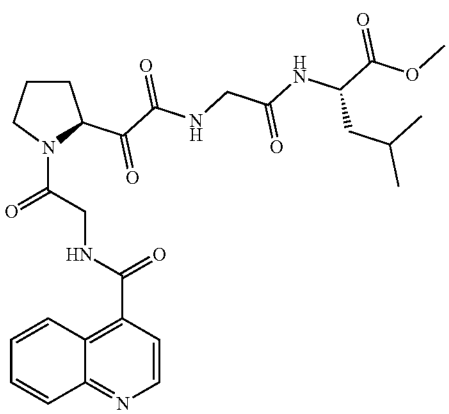 [SMILES: COC(=O)[C@H](CC(C)C)NC(=O)CNC(=O)C(=O)[C@@H]1CCCN1C(=O)CNC(=O)c1ccnc2ccccc12] | Methyl (2-oxo-2-((S)-1-((quinoline-4-carbonyl)glycyl)pyrrolidin-2-yl)acetyl)glycyl-L-leucinate |
| 19 | 5f | 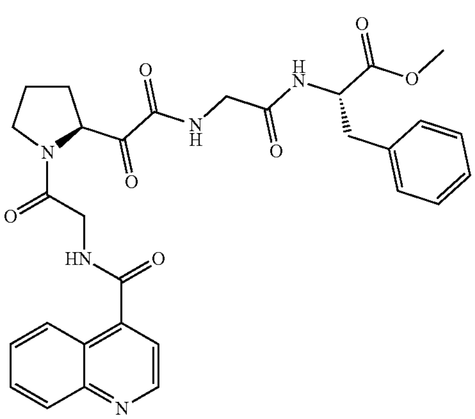 [SMILES: COC(=O)[C@H](Cc1ccccc1)NC(=O)CNC(=O)C(=O)[C@@H]1CCCN1C(=O)CNC(=O)c1ccnc2ccccc12] | Methyl (2-oxo-2-((S)-1-((quinoline-4-carbonyl)glycyl)pyrrolidin-2-yl)acetyl)glycyl-L-phenylalaninate |

| Example | Compound | Structure | Systematic name |
|---|---|---|---|
| 20 | 5g | 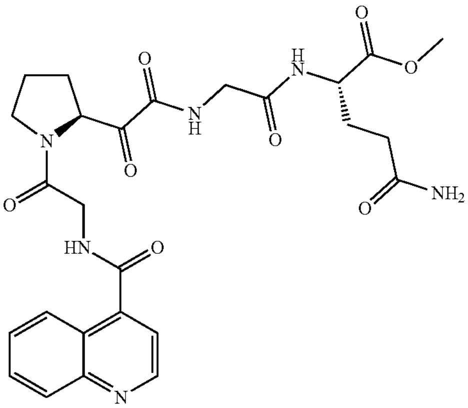 [SMILES: COC(=O)[C@H](CCC(N)=O)NC(=O)CNC(=O)C(=O)[C@@H]1CCCN1C(=O)CNC(=O)c1ccnc2ccccc12] | Methyl (2-oxo-2-((S)-1-((quinoline-4-carbonyl)glycyl)pyrrolidin-2-yl)acetyl)glycyl-L-glutaminate |
| 21 | 5h | 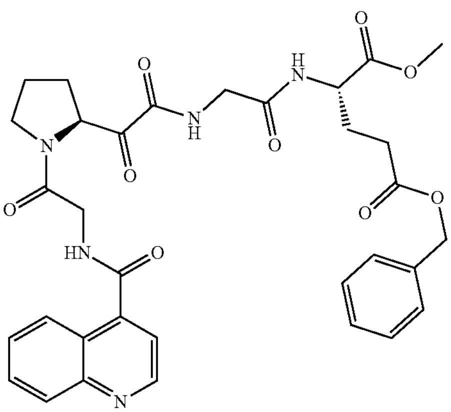 [SMILES: COC(=O)[C@H](CCC(=O)OCc1ccccc1)NC(=O)CNC(=O)C(=O)[C@@H]1CCCN1C(=O)CNC(=O)c1ccnc2ccccc12] | 5-Benzyl 1-methyl (2-oxo-2-((S)-1-((quinoline-4-carbonyl)glycyl)pyrrolidin-2-yl)acetyl)glycyl-L-glutamate |
| 22 | 5i | 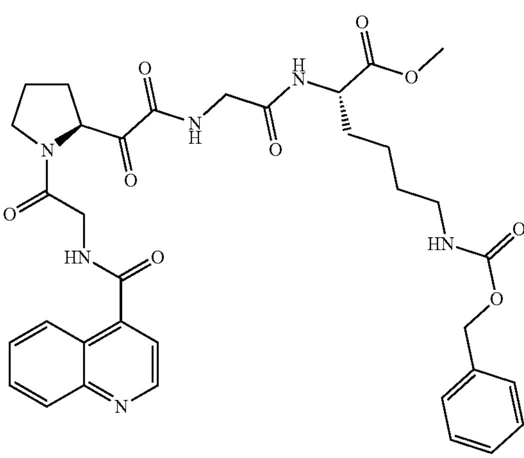 [SMILES: COC(=O)[C@H](CCCCNC(=O)OCc1ccccc1)NC(=O)CNC(=O)C(=O)[C@@H]1CCCN1C(=O)CNC(=O)c1ccnc2ccccc12] | Benzyl $N^6$-((benzyloxy)carbonyl)-$N^2$-((2-oxo-2-((S)-1-((quinoline-4-carbonyl)glycyl)pyrrolidin-2-yl)acetyl)glycyl)-L-lysinate |

| Example | Compound | Structure | Systematic name |
|---------|----------|-----------|-----------------|
| 23 | 9 | 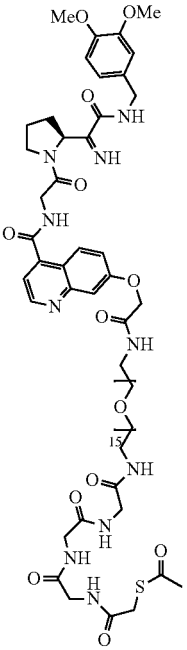 | (S)-S-(62-((4-((2-(2-(2-(3,4-dimethoxybenzyl)amino)-2-oxoacetyl)pyrrolidin-1-yl)-2-oxoethyl)carbamoyl)quinoline-7-yl)oxy)-2,5,8,11,61-pentaoxo-15,18,21,24,27,30,33,36,39,42,45,48,51,54,57-pentadecaoxa-3,6,9,12,60-pentaazadohexacontyl) ethanthioate |
| 24 | 12 | 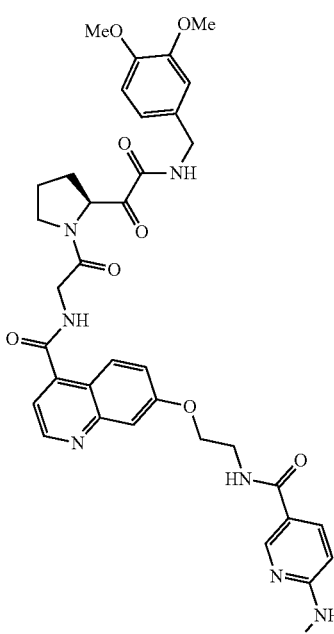 | (S)-N-(2-(2-(2-((3,4-dimethoxybenzyl)amino)-2-oxoacetyl)pyrrolidin-1-yl)-2-oxoethyl)-7-(2-(6-hydrazineylnicotinamido)ethoxy) quinoline-4-carboxamide |

General Procedure 1: Sequence of Passerini Reaction, Acid Deprotection and Basic Transacylation Boc-L-prolinal (1 eq.), N-Cbz-glycine (1 eq.) and the corresponding isonitrile (1 eq.) were dissolved in anhydrous DCM, and the resulting mixture was stirred at room temperature for 4 hours. At full conversion (LC-MS), trifluoroacetic acid was added and the mixture was stirred for another hour. The mixture was concentrated under reduced vacuum and then redissolved in DCM. While stirring and cooling to 0° C., triethylamine was added dropwise to the mixture. The mixture was further stirred at room temperature until full conversion (LC-MS, maximum 3 hours). The liquid portions of the mixture were evaporated under reduced pressure and the residue was redissolved in DCM. The polar portions of the mixture were extracted into water (3×) and the organic phase was dried over brine and sodium sulfate. After evaporating the solvent, α-hydroxyamide 4 was obtained, which was used for the next reaction without purification. Reaction yields are calculated based on the amount of Boc-L-prolinal used. In General Procedure 1, a mixture of diastereomers was always obtained, the retention times of which are given as $R_{t,1}$ and $R_{t,2}$.

General Procedure 2: Debenzylation

The Cbz or Bn protected substance was dissolved in methanol, and palladium hydroxide on coal was added to the mixture. The mixture was placed in a hydrogen atmosphere and stirred for 3 hours. The catalyst was separated from the mixture by filtration, and the liquid portion was concentrated under reduced pressure. Residual solvent and water were removed from the mixture under high vacuum. The substance obtained in this way was used without further purification for the next reaction.

General Procedure 3: Peptide-Forming Condensation Using TSTU

The carboxylic acid (1 eq.), TSTU (1 eq.) and DIPEA were dissolved in anhydrous DMF. After stirring for 1 hour at room temperature, a solution of the amine (1.1 eq.) in anhydrous DMF was added to the mixture, and the resulting mixture was stirred overnight. The product was isolated from the crude mixture by reversed-phase FLASH chromatography. Its trifluoroacetate salt was obtained by lyophilization of the fractions containing the desired product. Reaction yields are calculated with respect to the amount of precursor 4 used. In General Procedure 3, a mixture of diastereomers was always obtained, the retention times of which are reported as $R_{t,1}$ and $R_{t,2}$.

General Procedure 4: Oxidation

A mixture of α-hydroxyamide (1 eq.) and IBX (1.5 eq.) in DMSO was stirred overnight. At full conversion (by LC-MS), the product was isolated from the crude mixture by reversed-phase FLASH chromatography. Its trifluoroacetate salt was obtained by lyophilization of the fractions containing the desired product. Reaction yields are calculated with respect to the amount of α-hydroxyamide 5 used. According to the NMR and LC-MS analyses, the products of General Procedure 4 are present as a mixture of rotamers. Only the set of signals belonging to the dominant rotamer is listed in the NMR reports. The retention times of both rotamers are given as $R_{t,1}$ and $R_{t,2}$.

Preparation of Precursor 7

Methylester 2k (500 mg, 926 µmol) was dissolved in 9 ml of methanol and 1 ml of 10% (wt./wt.) aqueous KOH. After stirring at room temperature for 5 hours, the mixture was neutralized by the dropwise addition of 10% (wt./wt.) HCl to a pH between 7 and 8 and concentrated under reduced pressure. The product was isolated from the mixture directly by FLASH chromatography. Lyophilization of the fractions containing the desired product (LC-MS) gave the product trifluoroacetate as a white solid (350 mg, 72% yield; LC-MS $R_{t,1}$ 2.64 min, $R_{t,2}$ 2.71 min, m/z 415.30 $[M+H]^+$).

Example 1

(S)—N-(2-(2-(2-(Benzylamino)-2-oxoacetyl)pyrrolidin-1-yl)-2-oxoethyl)quinoline-4-carboxamide Precursor 1a (1163 mg, 79% yield; LC-MS $R_{t,1}$ 3.98 min, $R_{t,2}$ 4.03 min, m/z 426.36 $[M+H]^+$ was obtained from General Procedure 1. Precursor 1a was subsequently debenzylated by General Procedure 2, and the resulting amine was condensed with quinoline-4-carboxylic acid by General Procedure 3 to give precursor 2a (825 mg, 71% yield; LC-MS $R_{t,1}$ 3.36 min, $R_{t,2}$ 3.45 min, m/z 447.26 $[M+H]^+$). Precursor 2a was oxidized to the final α-ketoamide 3a (107 mg, 47% yield) by General Procedure 4.

$^1$H NMR (500 MHz, DMSO-$d_6$): 9.31 (bt, 1H, $J_{NH,CH2}$=6.4 Hz, COCONH); 9.04 (m, 1H, NH-2'); 9.04 (d, 1H, $J_{2,3}$=4.5 Hz, H-2); 8.35 (bdd, 1H, $J_{5,6}$=8.5 Hz, $J_{5,7}$=1.5 Hz, H-5); 8.11 (bd, 1H, $J_{5,7}$=8.5 Hz, H-8); 7.87 (ddd, 1H, $J_{7,8}$=8.5 Hz, $J_{8,7}$=6.9 Hz, $J_{7,5}$=1.5 Hz, H-7); 7.70 (ddd, 1H, $J_{6,5}$=8.5 Hz, $J_{6,7}$=6.9 Hz, $J_{6,8}$=1.3 Hz, H-6); 7.63 (d, 1H, $J_{3,2}$=4.5 Hz, H-3); 7.35-7.18 (m, 5H, H-o,n,p-Bn); 5.23 (dd, 1H, $J_{1'',2''}$=9.1 and 4.7 Hz, H-1"); 4.36 and 4.32 (2×dd, 2×1H, $J_{gem}$=14.8 Hz, $J_{CH2,NH}$=6.4 Hz, $CH_2$-Bn); 4.28 and 4.17 (2×dd, 2×11H, $J_{gem}$=16.8 Hz, $J_{2'NH}$=6.0 Hz, H-2'); 3.74-3.62 (m, 2H, H-4"); 2.25 (m, 1H, H-2'b); 2.03 (m, 1H, H-3"b); 1.97-1.80 (m, 2H, H-3"'a, 2"a);

$^{13}$C NMR (125.7 MHz, DMSO-$d_6$): 195.57 (COCONH); 166.92 (CO-1'); 166.56 (CO-3'); 160.60 (COCONH); 149.80 (CH-2); 146.60 (C-8a); 143.79 (C-4); 138.75 (C-i-Bn); 130.85 (CH-7); 128.56 (CH-m-Bn); 128.32 (CH-8); 127.97 (CH-6); 127.57 (CH-o-Bn); 127.20 (CH-p-Bn); 126.24 (CH-5); 124.58 (C-4a); 119.41 (CH-3); 60.47 (CH-1"); 46.12 ($CH_2$-4"); 42.31 ($CH_2$—Bn); 41.56 ($CH_2$-2'); 27.94 ($CH_2$-2"); 24.81 ($CH_2$-3');

LC-MS $R_{t,1}$ 3.49 min, $R_{t,2}$ 3.60 min, m/z 445.27 $[M+H]^+$; HR MS for $C_{25}H_{25}N_4O_4$ $[M+H]^+$ calculated 445.18703. found 445.18668.

Example 2

(S)—N-(2-(2-(2-((3,4-Dimethoxybenzyl)amino)-2-oxoacetyl)pyrrolidin-1-yl)-2-oxoethyl)quinoline-4-carboxamide Precursor 4d (1176 mg, 88% yield; LC-MS $R_{t,1}$ 3.79 min, $R_{t,2}$ 3.85 min, m/z 486.16 $[M+H]^+$) was obtained from General Procedure 1. Precursor 4d was subsequently debenzylated by General Procedure 2, and the resulting amine was condensed with quinoline-4-carboxylic acid by General Procedure 3 to give precursor 2b (130 mg, 92% yield; LC-MS $R_{t,1}$ 3.00 min, $R_{t,2}$ 3.07 min, m/z 507.25 $[M+H]^+$). Precursor 2b was oxidized to the final α-ketoamide 3b by General Procedure 4 (20 mg, 53% yield).

$^1$H NMR (500 MHz, DMSO-$d_6$): 9.22 (bt, 1H, $J_{NH,CH2}$=6.3 Hz, COCONH); 9.03-8.97 (m, 2H, NH-2', H-2); 8.32 (dd, 1H, $J_{5,6}$=8.4 Hz, $J_{5,7}$=1.4 Hz, H-5); 8.09 (bd, 1H, $J_{8,7}$=8.5 Hz, H-8); 7.83 (ddd, 1H, $J_{7,8}$=8.5 Hz, $J_{8,7}$=6.9 Hz, $J_{7,5}$=1.4 Hz, H-7); 7.66 (ddd, 1H, $J_{6,5}$=8.5 Hz, $J_{6,7}$=6.9 Hz, $J_{6,8}$=1.2 Hz, H-6); 7.57 (d, 1H, $J_{3,2}$=4.4 Hz, H-3); 6.91 (d, 1H, $J_{2,6}$=2.0 Hz, H-2-Ph); 6.86 (d, 1H, $J_{5,6}$=8.3 Hz, H-5-Ph); 6.79 (dd, 1H, $J_{6,5}$=8.2 Hz, $J_{6,2}$=2.0 Hz, H-6-Ph); 5.23 (dd, 1H, $J_{1'',2''}$=9.2 and 4.7 Hz, H-1"); 4.33-4.21 (m, 3H, $CH_2$-Ph, H-2'b); 4.15 (dd, 1H, $J_{gem}$=16.7 Hz, $J_{2'a,NH}$=5.9 Hz, H-2'a); 3.70 (s, 3H, $CH_3$O-3-Ph); 3.69 (s, 3H, $CH_3$O-4-Ph); 3.70-3.62 (m, 2H, H-4"); 2.24 (m, 1H, H-2'b); 2.01 (m, 1H, H-3"b); 1.90 (m, 1H, H-3"a); 1.84 (m, 1H, H-2"a);

$^{13}$C NMR (125.7 MHz, DMSO-$d_6$): 195.66 (COCONH); 167.08 (CO-1'); 166.56 (CO-3'); 160.48 (COCONH); 150.15 (CH-2); 148.75 (C-3-Ph); 148.05 (C-4-Ph); 147.42 (C-8a); 142.98 (C-4); 131.10 (C-1-Ph); 130.40 (CH-7); 128.89 (CH-8); 127.69 (CH-6); 126.14 (CH-5); 124.49 (C-4a); 119.75 (CH-6-Ph); 119.33 (CH-3); 111.84 (CH-5-Ph); 111.69 (CH-2-Ph); 60.40 (CH-1"); 55.70 and 55.58 ($CH_3$O); 46.12 ($CH_2$-4"'); 42.08 ($CH_2$-Ph); 41.54 ($CH_2$-2'); 27.95 ($CH_2$-2"); 24.81 ($CH_2$-3");

LC-MS $R_{t,1}$ 3.32 min, $R_{t,2}$ 3.44 min, m/z 505.22 $[M+H]^+$; HR MS for $C_{27}H_{29}N_4O_6$ $[M+H]^+$ calculated 505.20816. found 505.20740.

Example 3

(S)—N-(2-(2-(2-((4-Fluorobenzyl)amino)-2-oxoacetyl)pyrrolidin-1-yl)-2-oxoethyl)quinoline-4-carboxamide Precursor 1c (113 mg, 51% yield; LC-MS $R_{t,1}$ 4.08 min, $R_{t,2}$ 4.14 min, m/z 444.06 $[M+H]^+$) was obtained from General Procedure 1. Precursor 1c was subsequently debenzylated by General Procedure 2, and the resulting amine was condensed with quinoline-4-carboxylic acid by General Procedure 3 to give precursor 2c (70 mg, 74% yield; LC-MS $R_{t,1}$ 3.52 min, $R_{t,2}$ 3.61 min, m/z 465.01 [M+H]$^+$). Precursor 2c was oxidized to the final α-ketoamide 3c (37 mg, 65% yield) by General Procedure 4.

$^1$H NMR (500 MHz, DMSO-d$_6$): 9.32 (bt, 1H, $J_{NH,CH2}$=6.4 Hz, COCONH); 9.05 (t, 1H, $J_{NH,2'}$=6.0 Hz, NH-2'); 9.04 (d, 1H, $J_{2,3}$=4.5 Hz, H-2); 8.34 (dd, 1H, $J_{5,6}$=8.5 Hz, $J_{5,7}$=1.5 Hz, H-5); 8.11 (dm, 1H, $J_{5,7}$=8.5 Hz, H-8); 7.87 (ddd, 1H, $J_{7,8}$=8.5 Hz, $J_{8,7}$=6.9 Hz, $J_{7,5}$=1.5 Hz, H-7); 7.70 (ddd, 1H, $J_{6,5}$=8.5 Hz, $J_{6,7}$=6.9 Hz, $J_{6,8}$=1.3 Hz, H-6); 7.62 (d, 1H, $J_{3,2}$=4.5 Hz, H-3); 7.31 (m, 2H, H-o-Ph); 7.13 (m, 2H, H-m-Ph); 5.22 (dd, 1H, $J_{1'',2''}$=9.2 and 4.7 Hz, H-1''); 4.32 (bd, 2H, $J_{CH2,NH}$=6.5 Hz, CH$_2$-Ph); 4.27 and 4.17 (2×dd, 2×1H, $J_{gem}$=16.9 Hz, $J_{2',NH}$=6.0 Hz, H-2'); 3.71-3.62 (m, 2H, H-4''); 2.24 (m, 1H, H-2''b); 2.01 (m, 1H, H-3''b); 1.89. (m, 1H, H-3''a); 1.86 (m, 1H, H-2''a);

$^{13}$C NMR (125.7 MHz, DMSO-d$_6$): 195.56 (COCONH); 166.98 (CO-1'); 166.61 (CO-3'); 161.50 (d, $J_{C,F}$=242.6 Hz, C-p-Ph); 160.54 (COCONH); 149.87 (CH-2); 146.71 (C-8a); 143.72 (C-4); 134.99 (d, $J_{C,F}$=3.0 Hz, C-i-Ph); 130.84 (CH-7); 129.69 (d, $J_{C,F}$=8.2 Hz, CH-o-Ph); 128.33 (CH-8); 127.98 (CH-6); 126.25 (CH-5); 124.60 (C-4a); 119.43 (CH-3); 115.34 (d, $J_{C,F}$=21.3 Hz, CH-m-Ph); 60.51 (CH-1'); 46.16 (CH$_2$-4''); 41.66 (CH$_2$-Ph); 41.59 (CH$_2$-2'); 27.97 (CH$_2$-2''); 24.85 (CH$_2$-3'');

LC-MS $R_{t,1}$ 3.65 min, $R_{t,2}$ 3.78 min, m/z 462.99 [M+H]$^+$;
HR MS for $C_{25}H_{24}FN_4O_4$[M+H]$^+$ calculated 463.17761. found 463.17741.

Example 4

(S)—N-(2-Oxo-2-(2-(2-oxo-2-(fenethylamino)acetyl)pyrrolidin-1-yl)ethyl)quinoline-4-carboxamide Precursor 1d (380 mg, 85% yield; LC-MS $R_t$ 4.08 min, $R_{t,2}$ 4.14 min, m/z 440.32 [M+H]$^+$) was obtained from General Procedure 1. Precursor 1d was subsequently debenzylated by General Procedure 2, and the resulting amine was condensed with quinoline-4-carboxylic acid by General Procedure 3 to give Precursor 2d (286 mg, 68% yield; LC-MS $R_{t,1}$ 3.49 min, $R_{t,2}$ 3.59 min, m/z 461.30 [M+H]$^+$). Precursor 2d was oxidized to the final α-ketoamide 3d (74 mg, 67% yield) by General Procedure 4.

$^1$H NMR (500 MHz, DMSO-d$_6$): 9.02 (t, 1H, $J_{NH,2'}$=6.0 Hz, NH-2'); 9.01 (d, 1H, $J_{2,3}$=4.4 Hz, H-2); 8.83 (t, 1H, $J_{NH,CH2}$=6.0 Hz, COCONH); 8.34 (dm, 1H, $J_{5,6}$=8.5 Hz, H-5); 8.09 (dm, 1H, $J_{V,7}$=8.5 Hz, H-8); 7.84 (ddd, 1H, $J_{7,8}$=8.5 Hz, $J_{8,7}$=6.9 Hz, $J_{7,5}$=1.5 Hz, H-7); 7.68 (ddd, 1H, $J_{6,5}$=8.5 Hz, $J_{6,7}$=6.9 Hz, $J_{6,8}$=1.3 Hz, H-6); 7.58 (d, 1H, $J_{3,2}$=4.4 Hz, H-3); 7.28 (m, 2H, H-m-Ph); 7.23-7.16 (m, 3H, H-o,p-Ph); 5.20 (dd, 1H, $J_{1'',2''}$=9.1 and 4.6 Hz, H-1''); 4.26 and 4.16 (2×dd, 2×1H, $J_{gem}$=16.8 Hz, $J_{2',NH}$=6.0 Hz, H-2'); 3.70-3.62 (m, 2H, H-4''; 3.42-3.31 (m, 2H, CH$_2$CH$_2$-Ph); 2.78 (t, 2H, $J_{CH2,CH2}$=7.7 Hz, CH$_2$CH$_2$-Ph); 2.21 (m, 1H, H-2''b); 2.00 (m, 1H, H-3''b); 1.87 (m, 1H, H-3'''a); 1.77 (m, 1H, H-2''a);

$^{13}$C NMR (125.7 MHz, DMSO-d$_6$): 195.54 (COCONH); 167.10 (CO-1'); 166.58 (CO-3'); 160.39 (COCONH); 150.12 (CH-2); 147.29 (C-8a); 143.21 (C-4); 139.27 (C-i-Ph); 130.53 (CH-7); 128.88 (CH-o-Ph); 128.78 (CH-8); 128.61 (CH-m-Ph); 127.76 (CH-6); 126.44 (CH-p-Ph); 126.19 (CH-5); 124.53 (C-4a); 119.35 (CH-3); 60.51 (CH-1''); 46.11 (CH$_2$-4''); 41.58 (CH$_2$-2'); 40.44 (CH$_2$CH$_2$-Ph); 34.83 (CH$_2$CH$_2$-Ph); 27.83 (CH$_2$-2''); 24.72 (CH$_2$-3'');

LC-MS $R_{t,1}$ 3.63 min, $R_{t,2}$ 3.73 min, m/z 459.25 [M+H]$^+$;
HR MS for $C_{26}H_{25}N_4O_4$ [M+H]$^+$ calculated 459.20268. found 459.20258.

Example 5

(S)—N-(2-(2-(2-((3,4-Dimethoxyfenethyl)amino)-2-oxoacetyl)pyrrolidin-1-yl)-2-oxoethyl)quinoline-4-carboxamide Precursor 1e (LC-MS $R_{t,1}$ 3.85 min, $R_{t,2}$ 3.91 min, m/z 500.28 [M+H]$^+$) was obtained from General Procedure 1. Precursor 1e was subsequently debenzylated by General Procedure 2, and the resulting amine was condensed with quinoline-4-carboxylic acid by General Procedure 3 to give Precursor 2e (260 mg, 59% yield; LC-MS $R_{t,1}$ 3.28 min, $R_{t,2}$ 3.38 min, m/z 521.27 [M+H]$^+$). Precursor 2e was oxidized to the final α-ketoamide 3e (88 mg, 88% yield) by General Procedure 4.

$^1$H NMR (500 MHz, DMSO-d$_6$): 9.04 (d, 1H, $J_{2,3}$=4.5 Hz, H-2); 9.04 (m, 1H, NH-2'); 8.78 (bt, 1H, $J_{NH,CH2}$=6.0 Hz, COCONH); 8.36 (bdd, 1H, $J_{5,6}$=8.5 Hz, $J_{5,7}$=1.5 Hz, H-5); 8.11 (bd, 1H, $J_{8,7}$=8.4 Hz, H-8); 7.87 (ddd, 1H, $J_{7,8}$=8.5 Hz, $J_{8,7}$=6.9 Hz, $J_{7,5}$=1.5 Hz, H-7); 7.71 (ddd, 1H, $J_{6,5}$=8.5 Hz, $J_{6,7}$=6.9 Hz, $J_{6,8}$=1.3 Hz, H-6); 7.62 (d, 1H, $J_{3,2}$=4.5 Hz, H-3); 6.84 (d, 1H, $J_{5,6}$=8.2 Hz, H-5-Ph); 6.78 (d, 1H, $J_{2,6=2.0}$ Hz, H-2-Ph); 6.70 (dd, 1H, $J_{6,5}$=8.2 Hz, $J_{6,2}$=2.0 Hz, H-6-Ph); 5.21 (dd, 1H, $J_{1',2'}$=9.3 and 4.7 Hz, H-1''); 4.25 and 4.17 (2×dd, 2×1H, $J_{gem}$=16.8 Hz, $J_{2',NH}$=6.1 Hz, H-2'); 3.71 (s, 3H, CH$_3$O-3-Ph); 3.69 (s, 3H, CH$_3$O-4-Ph); 3.70-3.60 (m, 2H, H-4''); 3.35 (m, 2H, CH$_2$CH$_2$-Ph); 2.72 (t, 2H, $J_{CH2,CH2}$=7.4 Hz, CH$_2$CH$_2$-Ph); 2.21 (m, 1H, H-2''b); 2.00 (m, 1H, H-3'b); 1.85 (m, 1H, H-3''a); 1.77 (m, 1H, H-2'a);

$^{13}$C NMR (125.7 MHz, DMSO-d$_6$): 195.57 (COCONH); 166.92 (CO-1'); 166.54 (CO-3'); 160.37 (COCONH); 149.80 (CH-2); 148.78 (C-3-Ph); 147.45 (C-4-Ph); 146.60 (C-8a); 143.82 (C-4); 131.67 (C-1-Ph); 130.86 (CH-7); 128.22 (CH-8); 127.97 (CH-6); 126.26 (CH-5); 124.59 (C-4a); 120.65 (CH-6-Ph); 119.40 (CH-3); 112.60 (CH-2-Ph); 112.03 (CH-5-Ph); 60.52 (CH-1''); 55.68 (CH$_3$O-4-Ph); 55.54 (CH$_3$O-3-Ph); 46.10 (CH$_2$-4'); 41.58 (CH$_2$-2'); 40.57 (CH$_2$CH$_2$-Ph); 34.33 (CH$_2$CH$_2$-Ph); 27.82 (CH$_2$-2''); 24.70 (CH$_2$-3'');

LC-MS $R_{t,1}$ 3.41 min, $R_{t,2}$ 3.52 min, m/z 519.23 [M+H]$^+$;
HR MS for $C_{28}H_3N_4O_6$[M+H]$^+$ calculated 519.22381. found 519.22360.

Example 6

(S)—N-(2-(2-(2-((4-Methoxyphenyl)amino)-2-oxoacetyl)pyrrolidin-1-yl)-2-oxoethyl)quinoline-4-carboxamide Precursor 1f (325 mg, 79% yield; LC-MS $R_{t,1}$ 3.97 min, $R_{t,2}$ 4.04 min, m/z 464.26 [M+Na]$^+$) was obtained from General Procedure 1. Precursor 1f was subsequently debenzylated by General Procedure 2, and the resulting amine was condensed with quinoline-4-carboxylic acid by General Procedure 3 to give Precursor 2f (171 mg, 40% yield; LC-MS $R_{t,1}$ 3.32 min, $R_{t,2}$ 3.45 min, m/z 463.25 [M+H]$^+$). Precursor 2f was oxidized to the final α-ketoamide 3f (77 mg, 63% yield) by General Procedure 4.

$^1$H NMR (500 MHz, DMSO-d$_6$): 10.56 (s, 1H, NH-Ph); 9.04 (bt, 1H, $J_{7NH,2'}$=6.0 Hz, NH-2'), 9.01 (d, 1H, $J_{2,3}$=4.4 Hz, H-2); 8.33 (bdd, 1H, $J_{5,6}$=8.5 Hz, $J_{5,7}$=1.5 Hz, H-5); 8.09

(dm, 1H, $J_{8,7}$=8.5 Hz, H-8); 7.83 (ddd, 1H, $J_{7,8}$=8.5 Hz, $J_{8,7}$=6.9 Hz, $J_{7,5}$=1.5 Hz, H-7); 7.74 (m, 2H, H-o-Ph); 7.68 (ddd, 1H, $J_{6,5}$=8.5 Hz, $J_{6,7}$=6.9 Hz, $J_{6,8}$=1.3 Hz, H-6); 7.58 (d, 1H, $J_{3,2}$=4.4 Hz, H-3); 6.93 (m, 2H, H-m-Ph); 5.30 (dd, 1H, $J_{1'',2''}$=9.0 and 4.6 Hz, H-1''); 4.27 and 4.20 (2×dd, 2×1H, $J_{gem}$=16.9 Hz, $J_{2',NH}$=6.0 Hz, H-2'); 3.73 (s, 3H, CH$_3$O-Ph); 3.76-3.65 (m, 2H, H-4''); 2.29 (m, 1H, H-2''b); 2.04 (m, 1H, H-3''b); 2.00-1.89 (m, 2H, H-3'''a, H-2''a);

$^{13}$C NMR (125.7 MHz, DMSO-d$_6$): 195.68 (COCONH); 167.07 (CO-1'); 166.68 (CO-3'); 158.54 (COCONH); 156.35 (C-p-Ph); 150.06 (CH-2); 147.16 (C-8a); 143.28 (C-4); 130.75 (C-i-Ph); 130.57 (CH-7); 128.68 (CH-8); 127.79 (CH-6); 126.18 (CH-5); 124.52 (C-4a); 122.19 (CH-o-Ph); 119.36 (CH-3); 114.11 (CH-m-Ph); 60.38 (CH-1''); 55.42 (CH$_3$O-Ph); 46.19 (CH$_2$-4''); 41.56 (CH$_2$-2'); 28.12 (CH$_2$-2''); 24.94 (CH$_2$-3'');

LC-MS $R_{t,1}$ 3.48 min, $R_{t,2}$ 3.62 min, m/z 461.24 [M+H]$^+$; HR MS for C$_{25}$H$_{25}$N$_4$O$_5$ [M+H]$^+$ calculated 461.18195. found 461.18205.

Example 7

Methyl (S)-4-(2-oxo-2-(1-((quinoline-4-carbonyl)glycyl)pyrrolidin-2-yl)acetamido)benzoate Precursor 1g (LC-MS $R_{t,1}$ 4.03 min, $R_{t,2}$ 4.11 min, m/z 492.20 [M+Na]$^+$) was obtained from General Procedure 1. Precursor 1g was subsequently debenzylated by General Procedure 2, and the resulting amine was condensed with quinoline-4-carboxylic acid by General Procedure 3 to give Precursor 2g (137 mg, 32% yield; LC-MS $R_{t,1}$ 3.42 min, $R_{t,2}$ 3.57 min, m/z 491.21 [M+H]$^+$). Precursor 2g was oxidized to the final α-ketoamide 3g (76 mg, 72% yield) by General Procedure 4.

$^1$H NMR (500 MHz, DMSO-d$_6$): 10.98 (s, 1H, COCONH); 9.04 (t, 1H, $J_{NH,CH2}$=6.0 Hz, NH-2'); 9.00 (d, 1H, $J_{2,3}$=4.4 Hz, H-2); 8.30 (dm, 1H, $J_{5,6}$=8.5 Hz, H-5); 8.08 (dm, 1H, $J_{8,7}$=8.5 Hz, H-8); 8.00-7.93 (m, 4H, H-o,m-Ph); 7.82 (ddd, 1H, $J_{7,8}$=8.5 Hz, $J_{8,7}$=6.9 Hz, $J_{7,5}$=1.4 Hz, H-7); 7.65 (ddd, 1H, $J_{6,5}$=8.5 Hz, $J_{6,7}$=6.9 Hz, $J_{6,8}$=1.3 Hz, H-6); 7.57 (d, 1H, $J_{5,2}$=4.4 Hz, H-3); 5.26 (dd, 1H, $J_{1'',2''}$=8.9 and 4.7 Hz, H-1''); 4.27 (dd, 1H, $J_{gem}$=16.9 Hz, $J_{2',NH}$=5.9 Hz, H-2'b); 4.20 (dd, 1H, $J_{gem}$=16.7 Hz, $J_{2'a,NH}$=6.1 Hz, H-2'a); 3.83 (s, 3H, CH$_3$COO); 3.78-3.67 (m, 2H, H-4''); 2.29 (m, 1H, H-2''b); 2.09-1.94 (m, 3H, H-3'', H-2'a);

$^{13}$C NMR (125.7 MHz, DMSO-d$_6$): 195.08 (COCONH); 167.09 (CO-1'); 166.81 (CO-3'); 165.98 (CH$_3$COO); 159.46 (COCONH); 150.08 (CH-2); 147.23 (C-8a); 143.14 (C-4); 142.16 (C-i-Ph); 130.51 (CH-7); 130.41 (CH-m-Ph); 128.74 (CH-8); 127.74 (CH-6); 126.15 (CH-5); 125.49 (C-p-Ph); 124.50 (C-4a); 120.32 (CH-o-Ph); 119.35 (CH-3); 60.36 (CH-1''); 52.28 (CH$_3$COO); 46.21 (CH$_2$-4''); 41.53 (CH$_2$-2'); 28.16 (CH$_2$-2''); 25.07 (CH$_2$-3'');

LC-MS $R_{t,1}$ 3.60 min, $R_{t,2}$ 3.70 min, m/z 489.18 [M+H]$^+$; HR MS for C$_{26}$H$_{25}$N$_4$O$_6$ [M+H]$^+$ calculated 489.17686. found 489.17664.

Example 8

(S)—N-(2-(2-(2-(Cyclopropylamino)-2-oxoacetyl)pyrrolidin-1-yl)-2-oxoethyl)quinoline-4-carboxamide Precursor 1h (1608 mg, 75% yield; LC-MS $R_{t,1}$ 3.51. min, $R_{t,2}$ 3.58 min, m/z 376.34 [M+H]$^+$) was obtained from General Procedure 1. Precursor 1h was subsequently debenzylated by General Procedure 2, and the resulting amine was condensed with quinoline-4-carboxylic acid by General Procedure 3 to give precursor 2h (176 mg, 78% yield; LC-MS $R_{t,1}$ 2.85 min, $R_{t,2}$ 2.94 min, m/z 397.36 [M+H]$^+$). Precursor 2h was oxidized to the final α-ketoamide 3h (67 mg, 77% yield) by General Procedure 4.

$^1$H NMR (500 MHz, CDCl$_3$): 8.91 (d, 1H, $J_{2,3}$=4.3 Hz, H-2); 8.26 (bd, 1H, $J_{5,6}$=8.5 Hz, H-5); 8.12 (dm, 1H, $J_{8,7}$=8.5 Hz, H-8); 7.74 (ddd, 1H, $J_{7,8}$=8.5 Hz, $J_{5,7}$=6.9 Hz, $J_{7,5}$=1.4 Hz, H-7); 7.60 (ddd, 1H, $J_{6,5}$=8.5 Hz, $J_{6,7}$=6.9 Hz, $J_{6,5}$=1.3 Hz, H-6); 7.48 (d, 1H, $J_{3,2}$=4.3 Hz, H-3); 7.14 (bt, 1H, $J_{NH,2'}$=4.3 Hz, NH-2'); 7.00 (bd, 1H, $J_{NH,CH}$=3.9 Hz, NH-cp); 5.33 (dd, 1H, $J_{1'',2''}$=9.0 and 5.5 Hz, H-1''); 4.39 (dd, 1H, $J_{gem}$=17.7 Hz, $J_{2'b,NH}$=4.6 Hz, H-2'b); 4.29 (dd, 1H, $J_{gem}$=17.7 Hz, $J_{2'a,NH}$=4.0 Hz, H-2'a); 3.72-3.57 (m, 2H, H-4''); 2.76 (m, 1H, CH-cp); 2.39 (m, 1H, H-2'b); 2.16-1.92 (m, 3H, H-2''a, H-3''); 0.86-0.76 and 0.64-0.51 (2×m, 2×2H, CH$_2$-cp);

$^{13}$C NMR (125.7 MHz, CDCl$_3$): 194.42 (CO-1''); 167.15 (CO-1'); 166.11 (CO-3'); 160.47 (CONH-cp); 149.73 (CH-2); 148.58 (C-8a); 141.07 (C-4); 129.99 (CH-7); 129.77 (CH-8); 127.73 (CH-6); 125.26 (CH-5); 124.36 (C-4a); 118.78 (CH-3); 60.85 (CH-1''); 46.35 (CH$_2$-4''); 42.30 (CH$_2$-2'); 28.33 (CH$_2$-2''); 24.93 (CH$_2$-3''); 22.38 (CH-cp); 6.37 and 6.34 (CH$_2$-cp);

LC-MS $R_{t,1}$ 2.91 min, $R_{t,2}$ 3.04 min, m/z 395.34 [M+H]$^+$; HR MS for C$_{21}$H$_{23}$N$_4$O$_4$ [M+H]$^+$ calculated 395.17138. found 395.17106.

Example 9

(S)—N-(2-(2-(2-(Isopropylamino)-2-oxoacetyl)pyrrolidin-1-yl)-2-oxoethyl)quinoline-4-carboxamide Precursor 1i (225 mg, 60% yield; LC-MS $R_{t,1}$ 3.66 min, $R_{t,2}$ 3.73 min, m/z 378.38 [M+H]$^+$) was obtained from General procedure 1. Precursor 1i was subsequently debenzylated by General Procedure 2, and the resulting amine was condensed with quinoline-4-carboxylic acid by General Procedure 3 to give Precursor 2i (80 mg, 48% yield; LC-MS $R_{t,1}$ 3.00 min, $R_{t,2}$ 3.10 min, m/z 399.36 [M+H]$^+$). Precursor 2i was oxidized to the final α-ketoamide 3i (27 mg, 39% yield) by General Procedure 4.

$^1$H NMR (500 MHz, DMSO-d$_6$): 9.06 (m, 1H, NH-2'); 9.05 (d, 1H, $J_{2,3}$=4.5 Hz, H-2); 8.58 (bd, 1H, $J_{NH,CH}$=8.2 Hz, COCONH); 8.35 (dm, 1H, $J_{5,6}$=8.5 Hz, H-5); 8.12 (dm, 1H, $J_{8,7}$=8.5 Hz, H-8); 7.89 (ddd, 1H, $J_{7,8}$=8.5 Hz, $J_{7,6}$=6.9 Hz, $J_{7,5}$=1.5 Hz, H-7); 7.73 (ddd, 1H, $J_{6,5}$=8.5 Hz, $J_{6,7}$=6.9 Hz, $J_{6,8}$=1.3 Hz, H-6); 7.64 (d, 1H, $J_{3,2}$=4.5 Hz, H-3); 5.21 (dd, 1H, $J_{1'',2''}$=9.2 and 4.3 Hz, H-1'''); 4.25 (dd, 1H, $J_{gem}$=16.9 Hz, $J_{2b,NH}$=5.9 Hz, H-2'b); 4.17 (dd, 1H, $J_{gem}$=16.9 Hz, $J_{2'a,NH}$=6.0 Hz, H-2'a); 3.98-3.87 (m, 1H, (CH$_3$)$_2$CH); 3.72-3.61 (m, 2H, H-4''); 2.23 (m, 1H, H-2''b); 2.00 (m, 1H, H-3'b); 1.91-1.77 (m, 2H, H-2''a, H-3''a); 1.11 and 1.10 (2×d, 2×3H, (CH$_3$)$_2$CH);

$^{13}$C NMR (125.7 MHz, DMSO-d$_6$): 195.80 (COCONH); 166.94 (CO-1'); 166.54 (CO-3'); 159.66 (COCONH); 149.82 (CH-2); 146.58 (C-8a); 143.89 (C-4); 130.92 (CH-7); 128.21 (CH-8); 128.00 (CH-6); 126.28 (CH-5); 124.61 (C-4a); 119.42 (CH-3); 60.56 (CH-1''); 46.13 (CH$_2$-4''); 41.60 (CH$_2$-2'); 41.02 ((CH$_3$)$_2$CH); 27.95 (CH$_2$-2''); 24.74 (CH$_2$-3'); 22.07 ((CH$_3$)$_2$CH);

LC-MS $R_{t,1}$ 3.11 min, $R_{t,2}$ 3.22 min, m/z 397.35 [M+H]$^+$; HR MS for C$_{21}$H$_{25}$N$_4$O$_4$ [M+H]$^+$ calculated 397.18703. found 397.18665.

Example 10

(S)—N-(2-Oxo-2-(2-(2-oxo-2-(pentylamino)acetyl)pyrrolidin-1-yl)ethyl)quinoline-4-carboxamide Precursor 1j was obtained from General Procedure 1 (370 mg, 90% yield; LC-MS $R_{t,1}$ 4.11 min, $R_{t,2}$ 4.17 min, m/z 406.39 [M+H]+). Precursor 1j was subsequently debenzylated by General Procedure 2, and the resulting amine was condensed with quinoline-4-carboxylic acid by General Procedure 3 to give Precursor 2j (291 mg, 64% yield; LC-MS $R_{t,1}$ 3.50 min, $R_{t,2}$ 3.61 min, m/z 427.39 [M+H]+). Precursor 2j was oxidized to the final α-ketoamide 3j (98 mg, 70% yield) by General Procedure 4.

$^1$H NMR (500 MHz, DMSO-d$_6$): 9.03 (d, 1H, $J_{2,3}$=4.5 Hz, H-2); 9.03 (m, 1H, NH-2'); 8.74 (bt, 1H, $J_{NH,CH}$=6.0 Hz, COCONH); 8.35 (bdd, 1H, $J_{5,6}$=8.5 Hz, $J_{5,7}$=1.5 Hz, H-5); 8.11 (bd, 1H, $J_{8,7}$=8.5 Hz, H-8); 7.86 (ddd, 1H, $J_{7,8}$=8.5 Hz, $J_{8,7}$=6.9 Hz, $J_{7,5}$=1.5 Hz, H-7); 7.71 (ddd, 1H, $J_{6,5}$=8.5 Hz, $J_{6,7}$=6.9 Hz, $J_{6,8}$=1.3 Hz, H-6); 7.61 (d, 1H, $J_{3,2}$=4.5 Hz, H-3); 5.23 (bdd, 1H, $J_{1'',2''}$=9.3 and 4.5 Hz, H-1'); 4.26 and 4.22 (2×dd, 2×1H, $J_{gem}$=16.8 Hz, $J_{2,NH}$=6.0 Hz, H-2); 3.70-3.62 (m, 2H, H-4''); 3.19-3.06 (m, 2H, CH$_2$(CH$_2$)$_3$CH$_3$); 2.24 (m, 1H, H-2''b); 2.00 (m, 1H, H-3'b); 1.92-1.74 (m, 2H, H-3''a,2''a); 1.46 (m, 2H, CH$_2$CH$_2$(CH$_2$)$_2$CH$_3$); 1.32-1.17 (m, 4H, (CH$_2$)$_2$CH$_2$CH$_2$CH$_3$); 0.84 (t, 3H, $J_{CH3,CH2}$=7.1 Hz, (CH$_2$)$_4$CH$_3$);

$^{13}$C NMR (125.7 MHz, DMSO-d$_6$): 195.66 (COCONH); 166.96 (CO-1'); 166.52 (CO-3'); 160.42 (COCONH); 149.89 (CH-2); 146.81 (C-8a); 143.61 (C-4); 130.74 (CH-7); 128.39 (CH-8); 127.88 (CH-6); 126.23 (CH-5); 124.57 (C-4a); 119.38 (CH-3); 60.46 (CH-1''); 46.11 (CH$_2$-4''); 41.57 (CH$_2$-2'); 38.79 (CH$_2$(CH$_2$)$_3$CH$_3$); 28.75 ((CH$_2$)$_2$CH$_2$CH$_2$CH$_3$); 28.58 (CH$_2$CH$_2$(CH$_2$)$_2$CH$_3$); 27.91 (CH$_2$-2''); 24.73 (CH$_2$-3''); 22.00 ((CH$_2$)$_3$CH$_2$CH$_3$); 14.12 ((CH$_2$)$_4$CH$_3$);

LC-MS $R_{t,1}$ 3.63 min, $R_{t,2}$ 3.76 min, m/z 425.34 [M+H]+; HR MS for C$_{23}$H$_{29}$N$_4$O$_4$ [M+H]+ calculated 425.21833. found 425.21812.

Example 11

Methyl (S)-(2-oxo-2-(1-((quinoline-4-carbonyl)glycyl)pyrrolidin-2-yl)acetyl)glycinate Precursor 1k (800 mg, 95% yield; LC-MS $R_{t,1}$ 3.46 min, $R_{t,2}$ 3.51 min, m/z 408.32 [M+H]+) was obtained from General Procedure 1. Precursor 1k was subsequently debenzylated by General Procedure 2, and the resulting amine was condensed with quinoline-4-carboxylic acid by General Procedure 3 to give Precursor 2k (500 mg, 75% yield; LC-MS $R_{t,1}$ 2.84 min, $R_{t,2}$ 2.91 min, m/z 429.30 [M+H]+). Precursor 2k was oxidized to the final α-ketoamide 3k (15 mg, 46% yield) by General Procedure 4.

$^1$H NMR (500 MHz, DMSO-d$_6$): 9.10 (bt, 1H, $J_{NH,CH2}$=6.1 Hz, COCONH); 9.03 (t, 1H, $J_{NH,2'}$=6.1 Hz, NH-2'); 9.02 (d, 1H, $J_{2,3}$=4.4 Hz, H-2); 8.34 (dm, 1H, $J_{5,6}$=8.5 Hz, H-5); 8.10 (dm, 1H, $J_{5,7}$=8.5 Hz, H-8); 7.85 (ddd, 1H, $J_{7,8}$=8.5 Hz, $J_{8,7}$=6.9 Hz, $J_{7,5}$=1.4 Hz, H-7); 7.71 (ddd, 1H, $J_{6,5}$=8.5 Hz, $J_{6,7}$=6.9 Hz, $J_{6,8=1.3}$ Hz, H-6); 7.60 (d, 1H, $J_{3,2}$=4.4 Hz, H-3); 5.22 (dd, 1H, $J_{1''',2'''}$=9.2 and 4.5 Hz, H-1'''); 4.28 (dd, 1H, $J_{gem}$=16.9 Hz, $J_{2'b,NH}$=6.1 Hz, H-2'b); 4.17 (dd, 1H, $J_{gem}$=16.9 Hz, $J_{2'a,NH}$=6.0 Hz, H-2'a); 3.99-3.87 (m, 2H, CH$_3$COOCH$_2$); 3.72-3.60 (m, 2H, H-4''); 3.65 (s, 3H, CH$_3$COOCH$_2$); 2.25 (m, 1H, H-2''b); 2.02 (m, 1H, H-3''b); 1.88 (m, 1H, H-3'a); 1.84 (m, 1H, H-2'a);

$^{13}$C NMR (125.7 MHz, DMSO-d$_6$): 194.92 (COCONH). 169.62 (CH$_3$COO); 167.05 (CO-1'); 166.63 (CO-3'); 160.80 (COCONH); 150.02 (CH-2); 147.12 (C-8a); 143.31 (C-4); 130.58 (CH-7); 128.63 (CH-8); 127.82 (CH-6); 126.19 (CH-5); 124.53 (C-4a); 119.37 (CH-3); 60.52 (CH-1''); 52.18 (CH$_3$COO); 46.10 (CH$_2$-4''); 41.57 (CH$_2$-2'); 40.78 (CH$_3$COOCH$_2$); 27.79 (CH$_2$-2''); 24.72 (CH$_2$-3'');

LC-MS $R_{t,1}$ 2.90 min, $R_{t,2}$ 3.00 min, m/z 427.29 [M+H]+; HR MS for C$_{21}$H$_{23}$N$_4$O$_6$ [M+H]+ calculated 427.16121. found 427.16096.

Example 12 terc-Butyl (S)-(2-oxo-2-(1-((quinoline-4-carbonyl)glycyl)pyrrolidin-2-yl)acetyl)glycinate Precursor 1l (212 mg, 46% yield; LC-MS $R_{t,1}$ 3.51 min, $R_{t,2}$ 3.57 min, m/z 472.28 [M+Na]+) was obtained from General Procedure 1. Precursor 1l was subsequently debenzylated by General Procedure 2, and the resulting amine was condensed with quinoline-4-carboxylic acid by General Procedure 3 to give Precursor 2l (140 mg, 62% yield; LC-MS $R_{t,1}$ 3.40 min, $R_{t,2}$ 3.48 min, m/z 471.30 [M+H]+). Precursor 2l was oxidized to the final α-ketoamide 3l (55 mg, 50% yield) by General Procedure 4.

$^1$H NMR (500 MHz, DMSO-d$_6$): 9.07 (m, 1H, NH-2'); 9.06 (d, 1H, $J_{2,3}$=4.5 Hz, H-2); 9.00 (bt, 1H, $J_{NH,CH2}$=6.2 Hz, COCONH); 8.37 (bdd, 1H, $J_{5,6}$=8.5 Hz, $J_{5,7}$=1.5 Hz, H-5); 8.12 (dm, 1H, $J_{6,7}$=8.5 Hz, H-8); 7.88 (ddd, 1H, $J_{7,8}$=8.5 Hz, $J_{8,7}$=6.9 Hz, $J_{7,5}$=1.5 Hz, H-7); 7.74 (ddd, 1H, $J_{6,5}$=8.5 Hz, $J_{6,7}$=6.9 Hz, $J_{6,8}$=1.3 Hz, H-6); 7.65 (d, 1H, $J_{3,2}$=4.5 Hz, H-3); 5.23 (dd, 1H, $J_{1''',2'''}$=9.2 and 4.3 Hz, H-1'''); 4.29 (dd, 1H, $J_{gem}$=16.8 Hz, $J_{2'b,NH}$=6.1 Hz, H-2'b); 4.17 (dd, 1H, $J_{gem}$=16.8 Hz, $J_{2a,NH}$=5.9 Hz, H-2'a); 3.86-3.74 (m, 2H, CH$_2$COO); 3.72-3.62 (m, 2H, H-4''); 2.26 (m, 1H, H-2''b); 2.02 (m, 1H, H-3'b); 1.92-1.78 (m, 2H, H-3''a,2''a); 1.41 (s, 9H, (CH$_3$)$_3$C);

$^{13}$C NMR (125.7 MHz, DMSO-d$_6$): 195.02 (COCONH). 168.18 (CH$_2$COO); 166.90 (CO-1'); 166.59 (CO-3'); 160.76 (COCONH); 149.67 (CH-2); 146.27 (C-8a); 144.14 (C-4); 131.05 (CH-7); 128.13 (CH-6); 127.95 (CH-8); 126.32 (CH-5); 124.65 (C-4a); 119.46 (CH-3); 81.31 ((CH$_3$)$_3$C); 60.52 (CH-1''); 46.12 (CH$_2$-4''); 41.61 (CH$_2$-2'); 41.52 (CH$_2$COO); 27.92 ((CH$_3$)$_3$C); 27.83 (CH$_2$-2''); 24.71 (CH$_2$-3');

LC-MS $R_{t,1}$ 3.53 min, $R_{t,2}$ 3.62 min, m/z 469.29 [M+H]+; HR MS for C$_{24}$H$_{29}$N$_4$O$_6$ [M+H]+ calculated 469.20816. found 469.20798.

Example 13

Methyl (2-oxo-2-((S)-1-((quinoline-4-carbonyl)glycyl)pyrrolidin-2-yl)acetyl)alaninate General Procedure 1 gave precursor 1ma ((2-((S)-1-(((benzyloxy)carbonyl)glycyl)pyrrolidin-2-yl)-2-hydroxyacetyl)alanine; 237 mg, 82% yield; LC-MS $R_{t,1}$ 3.24 min, $R_{t,2}$ 3.34 min, m/z 408.27 [M+H]+), which was converted to the methyl ester by an esterification corresponding to General Procedure 3 using an excess of methanol instead of an amine (Precursor 1m; 100 mg, 44% yield; LC-MS $R_t$ 3.60 min, $R_{t,2}$ 3.66 min, m/z 422.36 [M+H]+). Precursor 1m was subsequently debenzylated by General Procedure 2, and the resulting amine was condensed with quinoline-4-carboxylic acid by General Procedure 3 to give Precursor 2m (76 mg, 58% yield; LC-MS $R_{t,1}$ 2.95 min, $R_{t,2}$ 3.03 min, $R_{t,2}$ 3.05 min, m/z 443.28 [M+H]+). Precursor 2m was oxidized to the final α-ketoamide 3m (49 mg, 87% yield) by General Procedure 4.

$^1$H NMR (500 MHz, DMSO-d$_6$): 9.13 and 9.12 (2×bd, 2×1H, $J_{NH,CH}$=7.5 Hz, COCONH); 9.06 (m, 2H, NH-2'); 9.06 (2×d, 2×1H, $J_{2,3}$=4.5 Hz, H-2); 8.38 and 8.36 (2×dm, 2×1H, $J_{5,6}$=8.6 Hz, H-5); 8.12 (2×dm, 2×1H, $J_{8,7}$=8.5 Hz, H-8); 7.89 and 7.88 (2×ddd, 2×1H, $J_{7,8}$=8.5 Hz, $J_{8,7}$=6.9 Hz, $J_{7,5}$=1.5 Hz, H-7); 7.75 and 7.73 (2×ddd, 2×1H, $J_{6,5}$=8.5 Hz, $J_{6,7}$=6.9 Hz, $J_{6,8}$=1.3 Hz, H-6); 7.65 and 7.64 (2×bd, 2×1H, $J_{3,2}$=4.5 Hz, H-3); 5.24 (dd, 1H, $J_{1'',2''}$=9.2 and 4.5 Hz, H-1''); 5.20 (dd, 1H, $J_{1'',2''}$=9.3 and 4.2 Hz, H-1''); 4.40 and 4.39 (2×pent, 2×1H, $J_{CH,NH}$=$J_{CH,CH3}$=7.4 Hz, CH$_3$CH); 4.28 and 4.27 (2×dd, 2×1H, $J_{gem}$=16.8 Hz, $J_{2'b,NH}$=6.0 Hz, H-2'b); 4.19 (2×dd, 2×1H, $J_{gem}$=16.8 Hz, $J_{2'a,NH}$=5.9 Hz, H-2'a); 3.75-3.60 (2×m, 2×2H, H-4''); 3.64 (2×s, 2×3H, CH$_3$COO); 2.30-2.20 (m, 2×1H, H-2''b); 2.06-1.96 (m, 2×1H, H-3''b); 1.93-1.77 (m, 4×1H, H-3''a, H-2''a); 1.36 and 1.34 (2×d, 2×3H, $J_{CH3,CH}$=7.3 Hz, CH$_3$CH);

$^{13}$C NMR (125.7 MHz, DMSO-d$_6$): 195.25 and 195.17 (COCONH); 172.49 (CH$_3$COO); 167.10 (CO-1'); 166.86 and 166.79 (CO-3'); 160.85 and 160.48 (COCONH); 149.90 and 149.88 (CH-2); 146.54 and 146.50 (C-8a); 144.39 and 144.29 (C-4); 131.27 and 131.24 (CH-7); 128.32 and 128.29 (CH-6); 128.22 and 128.16 (CH-8); 126.55 and 126.50 (CH-5); 124.86 and 124.85 (C-4a); 119.66 (CH-3); 61.10 and 60.62 (CH-1''); 52.59 and 52.56 (CH$_3$COO); 48.10 and 48.04 (CH$_3$CH); 46.32 (CH$_2$-4''); 41.84 and 41.80 (CH$_2$-2'); 28.03 and 27.96 (CH$_2$-2''); 24.94 and 24.88 (CH$_2$-3''); 16.95 and 16.84 (CH$_3$CH);

LC-MS $R_{t,1}$ 3.07 min, $R_{t,2}$ 3.15 min, m/z 441.25[M+H]$^+$;

Example 14

(S)—N-(2-(2-(2-((2-(Dimethylamino)-2-oxoethyl)amino)-2-oxoacetyl)pyrrolidin-1-yl)-2-oxoethyl)quinoline-4-carboxamide In successive General Procedures 3 and 4, α-ketoamide 5a (29 mg, 69% yield) was prepared from Precursor 7 and an ethanolic solution of dimethylamine (5.6 mol·l$^{-1}$).

$^1$H NMR (500 MHz, DMSO-d$_6$): 9.04 (m, 1H, NH-2'); 9.02 (d, 1H, $J_{2,3}$=4.5 Hz, H-2); 8.50 (bt, 1H, $J_{NH,CH2}$=5.5 Hz, COCONH); 8.34 (dm, 1H, $J_{5,6}$=8.5 Hz, H-5); 8.10 (dm, 1H, $J_{8,7}$=8.5 Hz, H-8); 7.85 (ddd, 1H, $J_{7,8}$=8.5 Hz, $J_{8,7}$=6.9 Hz, $J_{7,5}$=1.5 Hz, H-7); 7.71 (ddd, 1H, $J_{6,5}$=8.5 Hz, $J_{6,7}$=6.9 Hz, $J_{6,8}$=1.3 Hz, H-6); 7.61 (d, 1H, $J_{3,2}$=4.5 Hz, H-3); 5.24 (dd, 1H, $J_{1'',2''}$=9.2 and 4.2 Hz, H-1''); 4.29 (dd, 1H, $J_{gem}$=16.8 Hz, $J_{2'b,NH}$=6.2 Hz, H-2'b); 4.16 (dd, 1H, $J_{gem}$=16.8 Hz, $J_{2'a,NH}$=5.8 Hz, H-2'a); 4.03 and 3.98 (2×dd, 2×1H, $J_{gem}$=17.0 Hz, $J_{CH2,NH}$=5.7 Hz; CH$_2$CON); 3.72-3.61 (m, 2H, H-4''); 2.96 and 2.83 (2×s, 2×3H, (CH$_3$)$_2$N); 2.25 (m, 1H, H-2''b); 2.02 (m, 1H, H-3''b); 1.93-1.81 (m, 2H, H-3''a,2''a);

$^{13}$C NMR (125.7 MHz, DMSO-d$_6$): 195.18 (COCONH). 167.25 (CH$_2$CON); 167.05 (CO-1'); 166.64 (CO-3'); 160.26 (COCONH); 149.98 (CH-2); 146.99 (C-8a); 143.45 (C-4); 130.68 (CH-7); 128.53 (CH-8); 127.90 (CH-6); 126.22 (CH-5); 124.56 (C-4a); 119.41 (CH-3); 60.46 (CH-1''); 46.13 (CH$_2$-4''); 41.59 (CH$_2$-2'); 40.68 (CH$_2$CON); 35.86 and 35.34 ((CH$_3$)$_2$N); 27.77 (CH$_2$-2''); 24.72 (CH$_2$-3'');

LC-MS $R_{t,1}$ 2.79 min, $R_{t,2}$ 2.88 min, m/z 440.26 [M+H]$^+$;
HR MS for C$_{22}$H$_{26}$N$_5$O$_5$ [M+H]$^+$ calculated 440.19285. found 440.19275.

Example 15

(S)—N-(2-(2-(2-((2-(Ethyl(propyl)amino)-2-oxoethyl)amino)-2-oxoacetyl)pyrrolidin-1-yl)-2-oxoethyl)quinoline-4-carboxamide In successive General Procedures 3 and 4, α-ketoamide 5b (18 mg, 50% yield) was prepared from Precursor 7 and pyrrolidine.

$^1$H NMR (500 MHz, DMSO-d$_6$): 9.02 (m, 1H, NH-2'); 9.00 (d, 1H, $J_{2,3}$=4.4 Hz, H-2); 8.56 (bt, 1H, $J_{NH,CH2}$=5.7 Hz, COCONH); 8.33 (bdd, 1H, $J_{5,6}$=8.5 Hz, $J_{5,7}$=1.5 Hz, H-5); 8.09 (dm, 1H, $J_{8,7}$=8.5 Hz, H-8); 7.84 (ddd, 1H, $J_{7,5}$=8.5 Hz, $J_{8,7}$=6.9 Hz, $J_{7,5}$=1.5 Hz, H-7); 7.70 (ddd, 1H, $J_{6,5}$=8.5 Hz, $J_{6,7}$=6.9 Hz, $J_{6,8}$=1.3 Hz, H-6); 7.58 (d, 1H, $J_{3,2}$=4.4 Hz, H-3); 5.23 (dd, 1H, $J_{1'',2''}$=9.2 and 4.3 Hz, H-1''); 4.28 (dd, 1H, $J_{gem}$=16.8 Hz, $J_{2'b,NH}$=6.1 Hz, H-2'b); 4.15 (dd, 1H, $J_{gem}$=16.8 Hz, $J_{2'a,NH}$=5.8 Hz, H-2'a); 3.98-3.87 (m, 2H, CH$_2$CONH); 3.72-3.62 (m, 2H, H-4''); 3.41 and 3.29 (2×t, 2×2H, $J_{CH2,CH2}$=6.9 Hz; CH$_2$-2,5-C$_4$H$_8$N); 2.24 (m, 1H, H-2''b); 2.01 (m, 1H, H-3''b); 1.92-1.71 (m, 6H, H-3'a,2'a, H-3,4-C$_4$H$_8$N);

$^{13}$C NMR (125.7 MHz, DMSO-d$_6$): 195.21 (COCONH), 167.14 (CO-1'); 166.66 (CO-3'); 165.62 (CH$_2$CONH); 160.35 (COCONH); 150.17 (CH-2); 147.39 (C-8a); 143.06 (C-4); 130.47 (CH-7); 128.86 (CH-8); 127.77 (CH-6); 126.17 (CH-5); 124.51 (C-4a); 119.38 (CH-3); 60.52 (CH-1''); 46.14 (CH$_2$-4''); 45.89 and 45.15 (CH$_2$-2,5-C$_4$H$_8$N); 41.59 (CH$_2$-2'); 41.41 (CH$_2$CON); 27.78 (CH$_2$-2''); 25.81 (CH$_2$-3-C$_4$H$_8$N or CH$_2$-4-C$_4$H$_8$N); 24.73 (CH$_2$-3''); 23.94 81 (CH$_2$-3-C$_4$H$_8$N or CH$_2$-4-C$_4$H$_8$N);

LC-MS $R_{t,1}$ 2.98 min, $R_{t,2}$ 3.03 min, m/z 466.26 [M+H]$^+$;

Example 16

(S)—N-(2-(2-(2-((2-(Isopropylamino)-2-oxoethyl)amino)-2-oxoacetyl)pyrrolidin-1-yl)-2-oxoethyl)quinoline-4-carboxamide In successive General Procedures 3 and 4, α-ketoamide 5c (21 mg, 66% yield) was prepared from Precursor 7 and isopropylamine.

$^1$H NMR (500 MHz, DMSO-d$_6$): 9.02 (t, 1H, $J_{NH,2}$=6.0 Hz, NH-2'); 9.00 (d, 1H, $J_{2,3}$=4.4 Hz, H-2); 8.67 (t, 1H, $J_{NH,CH2}$=6.0 Hz, COCONH); 8.33 (ddd, 1H, $J_{5,6}$=8.5 Hz, $J_{5,7}$=1.5 Hz, $J_{5,8}$=0.6 Hz, H-5); 8.09 (dm, 1H, $J_{8,7}$=8.5 Hz, H-8); 7.84 (ddd, 1H, $J_{7,8}$=8.5 Hz, $J_{8,7}$=6.9 Hz, $J_{7,5}$=1.5 Hz, H-7); 7.83 (m, 1H, (CH$_3$)$_2$CHNH); 7.69 (ddd, 1H, $J_{6,5}$=8.5 Hz, $J_{6,7}$=6.9 Hz, $J_{6,8}$=1.3 Hz, H-6); 7.58 (d, 1H, $J_{3,2}$=4.4 Hz, H-3); 5.23 (dd, 1H, $J_{1'',2''}$=9.2 and 4.2 Hz, H-1''); 4.28 (dd, 1H, $J_{gem}$=16.8 Hz, $J_{2'b,NH}$=6.1 Hz, H-2'b); 4.17 (dd, 1H, $J_{gem}$=16.8 Hz, $J_{2'a,NH}$=5.9 Hz, H-2'a); 3.81 (m, 1H, (CH$_3$)$_2$CHNH); 3.76-3.62 (m, 4H, CH$_2$CONH, H-4''); 2.23 (m, 1H, H-2''b); 2.01 (m, 1H, H-3''b); 1.90-1.83 (m, 2H, H-3''a,2''a); 1.04 and 1.03 (2×d, 2×3H, $J_{CH3,CH}$=6.6 Hz, (CH$_3$)$_2$CHNH);

$^{13}$C NMR (125.7 MHz, DMSO-d$_6$): 195.05 (COCONH), 167.13 (CO-1'); 166.72 and 166.62 (CO-3', CH$_2$CONH); 160.47 (COCONH); 150.16 (CH-2); 147.44 (C-8a); 143.01 (C-4); 130.42 (CH-7); 128.89 (CH-8); 127.73 (CH-6); 126.17 (CH-5); 124.50 (C-4a); 119.35 (CH-3); 60.40 (CH-1''); 46.12 (CH$_2$-4''); 41.94 (CH$_2$CONH); 41.57 (CH$_2$-2'); 40.81 ((CH$_3$)$_2$CH); 27.75 (CH$_2$-2''); 24.72 (CH$_2$-3''); 22.58 ((CH$_3$)$_2$CH);

LC-MS $R_{t,1}$ 3.05 min, $R_{t,2}$ 3.11 min, m/z 454.24 [M+H]$^+$;
HR MS for C$_{23}$H$_{27}$N$_5$O$_5$ [M+H]$^+$ calculated 454.20850. found 454.20844.

Example 17

(S)—N-(2-(2-(2-((2-(Benzylamino)-2-oxoethyl)amino)-2-oxoacetyl)pyrrolidin-1-yl)-2-oxoethyl)quinoline-4-carboxamide In successive General Procedures 3 and 4, α-ketoamide 5d (10 mg, 19% yield) was prepared from Precursor 7 and benzylamine.

¹H NMR (500 MHz, DMSO-d₆): 9.01 (m, 1H, NH-2'); 8.99 (d, 1H, $J_{2,3}$=4.4 Hz, H-2); 8.85 (bt, 1H, $J_{NH,CH2}$=6.0 Hz, COCONH); 8.48 (bt, 1H, $J_{NH,CH2}$=6.0 Hz, NH—CH₂Bn); 8.33 (bdd, 1H, $J_{5,6}$=8.5 Hz, $J_{5,7}$=1.5 Hz, H-5); 8.09 (dm, 1H, $J_{8,7}$=8.5 Hz, H-8); 7.83 (ddd, 1H, $J_{7,8}$=8.5 Hz, $J_{8,7}$=6.9 Hz, $J_{7,5}$=1.5 Hz, H-7); 7.69 (ddd, 1H, $J_{6,5}$=8.5 Hz, $J_{6,7}$=6.9 Hz, $J_{6,8}$=1.3 Hz, H-6); 7.57 (d, 1H, $J_{3,2}$=4.4 Hz, H-3); 7.31 (m, 2H, H-m-Bn); 7.27-7.20 (m, 3H, H-o,p-Bn); 5.25 (dd, 1H, $J_{1'',2''}$=9.2 and 4.2 Hz, H-1''); 4.28 (m, 2H, CH₂—Bn); 4.27 (dd, 1H, $J_{gem}$=16.8 Hz, $J_{2'b,NH}$=6.0 Hz, H-2'b); 4.16 (dd, 1H, $J_{gem}$=16.8 Hz, $J_{2'a,NH}$=5.9 Hz, H-2'a); 3.86 (dd, 1H, $J_{gem}$=16.4 Hz, $J_{CH2,NH}$=6.3 Hz, CH₂CONH-b); 3.78 (dd, 1H, $J_{gem}$=16.4 Hz, $J_{CH2,NH}$=6.0 Hz, CH₂CONH-a); 3.71-3.62 (m, 2H, H-4''); 2.24 (m, 1H, H-2''b); 2.01 (m, 1H, H-3''b); 1.94-1.84 (m, 2H, H-3''a,2''a);

¹³C NMR (125.7 MHz, DMSO-d₆): 194.85 (COCONH); 168.01 (CH₂CONH); 167.13 (CO-1'); 166.62 (CO-3'); 160.56 (COCONH); 150.19 (CH-2); 147.49 (C-8a); 142.97 (C-4); 139.44 (C-i-Bn); 130.39 (CH-7); 128.94 (CH-8); 128.49 (CH-m-Bn); 127.70 (CH-6); 127.40 (CH-o-Bn); 127.02 (CH-p-Bn); 126.14 (CH-5); 124.49 (C-4a); 119.33 (CH-3); 60.44 (CH-1''); 46.11 (CH₂-4''); 42.28 (CH₂—Bn); 41.19 (CH₂CONH); 41.57 (CH₂-2'); 27.70 (CH₂-2''); 24.70 (CH₂-3'');

LC-MS $R_{t,1}$ 3.26 min, $R_{t,2}$ 3.35 min, m/z 502.21 [M+H]⁺; HR MS for $C_{27}H_{28}N_5O_5$ [M+H]⁺ calculated 502.20850. found 502.20825.

Example 18

Methyl(2-oxo-2-((S)-1-((quinoline-4-carbonyl)glycyl)pyrrolidin-2-yl)acetyl)glycyl-L-leucinate In successive General Procedures 3 and 4, α-ketoamide 5e (33 mg, 77% yield) was prepared from Precursor 7 and methyl-L-leucinate.

¹H NMR (500 MHz, DMSO-d₆): 9.05 (m, 1H, NH-2'); 9.05 (d, 1H, $J_{2,3}$=4.5 Hz, H-2); 8.77 (bt, 1H, $J_{NH,CH2}$=6.2 Hz, COCONH); 8.40 (bd, 1H, $J_{NH,CH}$=7.9 Hz, CH₃COOCHNH); 8.36 (dm, 1H, $J_{5,6}$=8.5 Hz, H-5); 8.12 (dm, 11H, $J_{8,7}$=8.5 Hz, H-8); 7.87 (ddd, 1H, $J_{7,8}$=8.5 Hz, $J_{8,7}$=6.9 Hz, $J_{7,5}$=1.5 Hz, H-7); 7.74 (ddd, 1H, $J_{6,5}$=8.4 Hz, $J_{6,7}$=6.9 Hz, $J_{6,8}$=1.3 Hz, H-6); 7.64 (d, 1H, $J_{3,2}$=4.5 Hz, H-3); 5.25 (dd, 1H, $J_{1'',2''}$=9.3 and 4.0 Hz, H-1''); 4.31 (m, 1H, CH₃COOCHNH); 4.28 (dd, 1H, $J_{gem}$=16.8 Hz, $J_{2'b,NH}$=6.1 Hz, H-2'b); 4.17 (dd, 1H, $J_{gem}$=16.8 Hz, $J_{2'a,NH}$=5.8 Hz, H-2'a); 3.86-3.75 (m, 2H, CH₂CONH); 3.72-3.62 (m, 2H, H-4''); 3.62 (s, 3H, CH₃COOCH); 2.23 (m, 1H, H-2''b); 2.01 (m, 1H, H-3'b); 1.92-1.83 (m, 2H, H-3''a,2''a); 1.60 (m, 11H, CH₂CH(CH₃)₂); 1.55 and 1.48 (2×m, 2×1H, CH₂CH(CH₃)₂); 0.87 and 0.83 (2×d, 2×3H, $J_{CH3,CH}$=6.5 Hz, CH₂CH(CH₃)₂);

¹³C NMR (125.7 MHz, DMSO-d₆): 194.80 (COCONH); 173.16 (CH₃COOCH); 168.13 (CH₂CONH); 166.92 (CO-1'); 166.57 (CO-3'); 160.48 (COCONH); 149.74 (CH-2); 146.46 (C-8a); 143.96 (C-4); 130.93 (CH-7); 128.06 (CH-6); 128.00 (CH-8); 126.28 (CH-5); 124.62 (C-4a); 119.43 (CH-3); 60.47 (CH-1''); 52.14 (CH₃COOCH); 50.45 (CH₃COOCH); 46.12 (CH₂-4''); 41.75 (CH₂CONH); 41.60 (CH₂-2'); 40.12 (CH₂CH(CH₃)₂); 27.64 (CH₂-2''); 24.65 (CH₂-3''); 24.35 (CH₂CH(CH₃)₂); 22.98 and 21.49 (CH₂CH(CH₃)₂);

LC-MS $R_{t,1}$ 3.46 min, $R_{t,2}$ 3.52 min, m/z 540.26 [M+H]⁺; HR MS for $C_{27}H_{34}N_5O_7$ [M+H]⁺ calculated 540.24527. found 540.24499.

Example 19

Methyl(2-oxo-2-((S)-1-((quinoline-4-carbonyl)glycyl)pyrrolidin-2-yl)acetyl)glycyl-L-phenylalaninate In successive General Procedures 3 and 4, α-ketoamide 5f (45 mg, 79% yield) was prepared from Precursor 7 and methyl-L-phenylalaninate.

¹H NMR (500 MHz, DMSO-d₆): 9.04 (m, 1H, NH-2'); 9.04 (d, 1H, $J_{2,3}$=4.5 Hz, H-2); 8.74 (bt, 1H, $J_{NH,CH2}$=6.2 Hz, COCONH); 8.50 (bd, 1H, $J_{NH,CH}$=7.7 Hz, CH₃COOCHNH); 8.35 (dm, 1H, $J_{5,6}$=8.5 Hz, H-5); 8.11 (dm, 1H, $J_{8,7}$=8.5 Hz, H-8); 7.87 (ddd, 1H, $J_{7,8}$=8.5 Hz, $J_{8,7}$=6.9 Hz, $J_{7,5}$=1.5 Hz, H-7); 7.73 (ddd, 1H, $J_{6,5}$=8.5 Hz, $J_{6,7}$=6.9 Hz, $J_{6,8}$=1.3 Hz, H-6); 7.63 (d, 1H, $J_{3,2}$=4.5 Hz, H-3); 7.27 (m, 2H, H-n-Bn); 7.23-7.18 (m, 3H, H-o,p-Bn); 5.24 (dd, 1H, $J_{1'',2''}$=9.2 and 4.1 Hz, H-1''); 4.47 (m, 1H, CH₃COOCH); 4.28 (dd, 1H, $J_{gem}$=16.8 Hz, $J_{2'b,NH}$=6.1 Hz, H-2'b); 4.17 (dd, 1H, $J_{gem}$=16.8 Hz, $J_{2'a,NH}$=5.9 Hz, H-2'a); 3.82 (dd, 1H, $J_{gem}$=16.6 Hz, $J_{CH2,NH}$=6.3 Hz, CH₂CONH-b); 3.72 (dd, 1H, $J_{gem}$=16.6 Hz, $J_{CH2,NH}$=6.1 Hz, CH₂CONH-a); 3.71-3.61 (m, 2H, H-4''); 3.60 (s, 3H, CH₃COO); 3.02 (dd, 1H, $J_{gem}$=13.7 Hz, $J_{CH2,CH}$=5.7 Hz, CH₂-Bn-b); 2.91 (dd, 1H, $J_{gem}$=13.7 Hz, $J_{CH2,CH}$=9.0 Hz, CH₂-Bn-a); 2.24 (m, 1H, H-2''b); 2.01 (m, 1H, H-3''b); 1.90-1.82 (m, 2H, H-3'a,2''a);

¹³C NMR (125.7 MHz, DMSO-d₆): 194.88 (COCONH); 172.09 (CH₃COO); 168.08 (CH₂CONH); 166.92 (CO-1'); 166.56 (CO-3'); 160.41 (COCONH); 149.75 (CH-2); 146.50 (C-8a); 143.89 (C-4); 137.21 (C-i-Bn); 130.90 (CH-7); 129.34 (CH-o-Bn); 128.53 (CH-m-Bn); 128.13 (CH-8); 128.03 (CH-6); 126.86 (CH-p-Bn); 126.27 (CH-5); 124.60 (C-4a); 119.42 (CH-3); 60.44 (CH-1''); 53.94 (CH₃COOCH); 52.16 (CH₃COO); 46.10 (CH₂-4''); 41.67 (CH₂CONH); 41.59 (CH₂-2'); 36.85 (CH₂—Bn); 27.70 (CH₂-2''); 24.68 (CH₂-3'');

LC-MS $R_{t,1}$ 3.52 min, $R_{t,2}$ 3.59 min, m/z 574.28 [M+H]⁺; HR MS for $C_{30}H_{32}N_5O_7$ [M+H]⁺ calculated 574.22962. found 574.22949.

Example 20

Methyl(2-oxo-2-((S)-1-((quinoline-4-carbonyl)glycyl)pyrrolidin-2-yl)acetylglycyl-L-glutaminate In successive General Procedures 3 and 4, α-ketoamide 5g (13 mg, 47% yield; LC-MS $R_{t,1}$ 2.69 min, $R_{t,2}$ 2.78 min, m/z 555.25 [M+H]⁺) was prepared from Precursor 7 and methyl-L-glutaminate.

Example 21

5-Benzyl 1-methyl (2-oxo-2-((S)-1-((quinoline-4-carbonyl)glycyl)pyrrolidin-2-yl)acetyl)glycyl-L-glutamate In successive General Procedures 3 and 4, α-ketoamide 5h (5 mg, 43% yield; LC-MS $R_{t,1}$ 3.68 min, $R_{t,2}$ 3.78 min, m/z 646.28 [M+H]⁺) was prepared from Precursor 7 and 5-benzyl-1-methyl-L-glutamate.

Example 22

Benzyl N⁶-((benzyloxy)carbonyl)-N²-((2-oxo-2-((S)-1-((quinoline-4-carbonyl)glycyl)pyrrolidin-2-yl)acetyl)glycyl)-L-lysinate In successive General Procedures 3 and 4, α-ketoamide 5i (15 mg, 60% yield) was prepared from Precursor 7 and methyl N6-Cbz-L-lysinate.

¹H NMR (500 MHz, DMSO-$d_6$): 9.02 (m, 1H, NH-2'); 9.01 (d, 1H, $J_{2,3}$=4.5 Hz, H-2); 8.76 (bt, 1H, $J_{NH,CH2}$=6.2 Hz, COCONH); 8.39 (bd, 1H, $J_{NH,CH}$=7.5 Hz, CH₃COOCHNH); 8.33 (dm, 1H, $J_{5,6}$=8.5 Hz, H-5); 8.09 (dm, 1H, $J_{8,7}$=8.5 Hz, H-8); 7.84 (ddd, 1H, $J_{7,8}$=8.5 Hz, $J_{8,7}$=6.9 Hz, $J_{7,5}$=1.5 Hz, H-7); 7.70 (m, 1H, H-6); 7.59 (d, 1H, $J_{3,2}$=4.5 Hz, H-3); 7.39-7.27 (m, 5H, H-o,ni,p-Ph); 7.26 (m, 1H, NH-5'''); 5.24 (dd, 1H, $J_{1''',2''}$=9.2 and 4.0 Hz, H-1'''); 5.00 (s, 2H, COOCH₂Ph); 4.28 (dd, 1H, $J_{gem}$=16.9 Hz, $J_{2'b,NH}$=6.1 Hz, H-2'b); 4.22 (m, 1H, CH-1'''); 4.16 (dd, 1H, $J_{gem}$=16.9 Hz, $J_{2'a,NH}$=6.0 Hz, H-2'a); 3.86-3.76 (m, 2H, CH₂CONH); 3.70-3.61 (m, 2H, H-4''); 3.62 (s, 3H, CH₃COO); 2.97 (m, 2H, H-5'''); 2.22 (m, 1H, H-2''b); 2.00 (m, 1H, H-3''b); 1.92-1.83 (m, 2H, H-3'a,2''a); 1.59 (m, 2H, CH₂-2'''); 1.38 (m, 2H, CH₂-4'''); 1.26 (m, 2H, CH₂-3''');

¹³C NMR (125.7 MHz, DMSO-$d_6$): 194.84 (COCONH); 172.74 (CH₃COO); 168.12 (CH₂CONH); 167.05 (CO-1'); 166.57 (CO-3'); 160.46 (COCONH); 156.30 (COOCH₂Ph); 150.07 (CH-2); 147.17 (C-8a); 143.25 (C-4); 137.48 (C-i-Ph); 130.53 (CH-7); 128.67 (CH-8); 128.57 (CH-n-Ph); 127.97 (CH-o,p-Ph); 127.79 (CH-6); 126.18 (CH-5); 124.51 (C-4a); 119.34 (CH-3); 65.33 (COOCH₂Ph); 60.43 (CH-1'''); 52.12 and 52.09 (CH₃COO, CH-1'''); 46.09 (CH₂-4'''); 41.71 (CH₂CONH); 41.57 (CH₂-2'); 40.25 (CH₂-5'''); 30.82 (CH₂-2'''); 29.14 (CH₂-4'''); 27.65 (CH₂-2'''); 24.65 (CH₂-3'''), 22.75 (CH₂-3''');

LC-MS $R_{t,1}$ 3.72 min, $R_{t,2}$ 3.79 min, m/z 689.29 [M+H]⁺;
HR MS for $C_{35}H_{41}N_6O_9$[M+H]⁺ calculated 689.29295. found 689.29276.

Example 23

(S)—S-(62-((4-((2-(2-(2-((3,4-dimethoxybenzyl)amino)-2-oxoacetyl)pyrrolidin-1-yl)-2-oxoethyl)carbamoyl)quinoline-7-yl)oxy)-2,5,8,11,61-pentaoxo-15,18,21,24,27,30,33,36,39,42,45,48,51,54,57-pentadecaoxa-3,6,9,12,60-pentaazadohexacontyl) ethanthioate Precursor 1b was debenzylated by General Procedure 2, and the resulting amine was condensed by General Procedure 3 with quinoline-4-carboxylic acid derivative 10 to give Precursor 11 (417 mg, 65% yield; LC-MS $R_{t,1}$ 3.76 min, $R_{t,2}$ 3.82 min, m/z 642.59 [½(M-COOtBu)+H]⁺). Precursor 11 was oxidized to α-ketoamide (229 mg, 55% yield; LC-MS $R_{t,1}$ 3.81 min, $R_{t,2}$ 3.87 min, m/z 641.57 [½(M-COOtBu)+H]⁺) by General Procedure 4. The product was then deprotected in 10 ml of 30% TFA in DCM. The liquid components were evaporated under reduced pressure, and the resulting amine was isolated by FLASH chromatography. After lyophilization of the product-containing fractions, this amine was condensed by General Procedure 3 with Boc-Gly-Gly-Gly (41 mg, 22% yield; LC-MS Ru 3.51 min, $R_{t,2}$ 3.57 min, m/z 727.06 [½(M-COOtBu)+H]⁺). The deprotection step under TFA/DCM conditions mentioned above was repeated, and the resulting amine was condensed by General Procedure 3 with S-acetyl-2-thioacetic acid to give the final Product 12. (2.2 mg, 28% yield; LC-MS $R_{t,1}$ 3.42 min, $R_{t,2}$ 3.47 min, m/z 785.10 [½M+H]⁺).

Example 24

(S)—N-(2-(2-(2-((3,4-dimethoxybenzyl)amino)-2-oxoacetyl)pyrrolidin-1-yl)-2-oxoethyl)-7-(2-(6-hydrazinylnicotinamido)ethoxy)quinoline-4-carboxamide Precursor 1b was debenzylated by General Procedure 2 and the resulting amine was condensed by General Procedure 3 with quinoline-4-carboxylic acid derivative 13 to give Precursor 14 (170 mg, 46% yield; LC-MS $R_{t,1}$ 3.61 min, $R_{t,2}$ 3.68 min, m/z 666.30 [M+H]⁺). Precursor 14 was oxidized to α-ketoamide (121 mg, 72% yield; LC-MS $R_{t,1}$ 3.71 min, $R_{t,2}$ 3.78 min, m/z 664.26 [M+H]⁺) by General Procedure 4. The product was then deprotected in 7 ml of 30% TFA in DCM. The liquid components were evaporated under reduced pressure, and the resulting amine was isolated by FLASH chromatography. After lyophilization of the product-containing fractions, this amine was condensed by General Procedure 3 with N-Boc-hydrazinonicotinic acid (24 mg, 59% yield; LC-MS $R_{t,1}$ 3.41 min, $R_{t,2}$ 3.48 min, m/z 799.31 [M+H]⁺). The deprotection step under TFA/DCM conditions mentioned above was repeated to give the final Product 15 (1 mg, 8% yield; LC-MS $R_{t,1}$ 2.88 min, $R_{t,2}$ 2.96 min, m/z 699.20 [M+H]⁺).

Example 25

Measuring the Inhibitory Activity of α-Ketoamide Inhibitors

The human recombinant FAP enzyme was prepared according to a previously published procedure (Dvofdkovi et al. 2017, *J. Med. Chem.*, 8365). The human recombinant enzymes DPPIV and PREP were purchased from R&D Systems (cat. numbers 9168-SE-010 and 4308-SE-010). $IC_{50}$ values were measured in duplicate according to a previously published procedure (Dvořáková et al. 2017, *J. Med. Chem.*, 8365). Data were analysed by nonlinear regression with GraphPrism (version 8.3.1). The measurement results are given as values of the mean inhibitory concentration $IC_{50}$ and its linearized form via the negative decimal logarithm of $pIC_{50}$. The most active substances exhibit the lowest $IC_{50}$ and $pIC_{50}$ values.

Results of Measuring the Inhibitory Activities of Substances Against FAP

| Example | Compound | $pIC_{50}$ [mol · l⁻¹] | $IC_{50}$ [nmol · l⁻¹] | 95% confidence interval $IC_{50}$ [nmol · l⁻¹] Min | Max |
|---|---|---|---|---|---|
| 1 | 3a | 8.27 ± 0.04 | 5.336 | 4.488 | 6.437 |
| 2 | 3b | 9.72 ± 0.03 | 0.1909 | 0.165 | 0.2205 |
| 3 | 3c | 8.36 ± 0.04 | 4.41 | 3.636 | 5.378 |
| 4 | 3d | 8.34 ± 0.02 | 4.605 | 4.121 | 5.170 |
| 5 | 3e | 8.84 ± 0.03 | 1.459 | 1.232 | 1.730 |
| 6 | 3f | 8.17 ± 0.04 | 6.814 | 5.632 | 8.691 |
| 7 | 3g | 8.50 ± 0.02 | 3.157 | 2.821 | 3.541 |
| 8 | 3h | 8.37 ± 0.03 | 4.255 | 3.683 | 4.945 |
| 9 | 3i | 7.68 ± 0.02 | 20.75 | 18.44 | 23.46 |
| 10 | 3j | 8.53 ± 0.03 | 2.988 | 2.539 | 3.534 |
| 11 | 3k | 8.10 ± 0.05 | 7.932 | 6.373 | 10.68 |
| 12 | 3l | 9.57 ± 0.02 | 0.2676 | 0.2445 | 0.2952 |
| 13 | 3m | 8.53 ± 0.02 | 2.97 | 2.712 | 3.255 |
| 14 | 5a | 7.81 ± 0.03 | 15.6 | 13.75 | 17.92 |
| 15 | 5b | 8.14 ± 0.03 | 7.246 | 6.234 | 8.468 |
| 16 | 5c | 8.04 ± 0.03 | 9.08 | 7.738 | 10.75 |
| 17 | 5d | 8.39 ± 0.03 | 4.053 | 3.374 | 4.885 |
| 18 | 5e | 7.49 ± 0.04 | 32.74 | 27.41 | 39.39 |
| 19 | 5f | 8.56 ± 0.03 | 2.778 | 2.395 | 3.234 |
| 20 | 5g | 7.74 ± 0.03 | 18.42 | 15.55 | 21.99 |
| 21 | 5h | 9.23 ± 0.05 | 0.5895 | 0.4548 | 0.7803 |
| 22 | 5i | 8.70 ± 0.04 | 1.986 | 1.588 | 2.567 |

Results of Measurement of Inhibitory Activities of Reference Substances According to Formulas a and B Against FAP, DPPIV and PREP

| Substance according to the formula | $pIC_{50}$ [mol·l$^{-1}$] | FAP$^a$ | DPPIV$^a$ IC$_{50}$ [nmol·l$^{-1}$] | PREP$^a$ |
|---|---|---|---|---|
| A | 7.55 ± 0.05 | 28.53 | >4000 | 660 |
| B | 8.37 ± 0.01 | 4.273 | >4000 | 670 |

Results of Measurement of Inhibitory Activities of Selected Substances Against DPPIV and PREP

| Example | Compound | DPPIV IC$_{50}$ [nmol·l$^{-1}$] | PREP | FAP/PREP selectivity index Calculted as IC$_{50}$(PREP)/IC$_{50}$(FAP) |
|---|---|---|---|---|
| 2 | 3b | >4000 | 0.4 | 2.1 |
| 5 | 3e | >4000 | 0.5 | 0.34 |
| 10 | 3j | >4000 | 0.4 | 0.13 |
| 12 | 3l | >4000 | 0.6 | 2.2 |
| 19 | 5f | >4000 | 0.3 | 0.0092 |
| 22 | 5i | >4000 | 0.26 | 0.54 |

Example 26

Measurement of Stability of α-Ketoamide Inhibitors

Stability in Plasma

A 10 mmol·l$^{-1}$ solution in DMSO was prepared from each test substance, 0.7 μl of the solution was added to 1400 μl of human (Biowest) or murine (Biosera) plasma maintained at 37° C., After 0, 20, 60 and 120 minutes, 40 μl aliquots were taken and analysed by LC-MS:

An aliquot of plasma was extracted with 120 μl of methanol containing caffeine as an internal standard. The solution was vortexed (5 min) and centrifuged (20500 g; 10 min), the supernatant was transferred to a vial, and 1 μl of the mixture was used for LC-MS analysis.

Stability in Microsomes

Murine microsomes (Thermofisher) 0.5 mg/ml were incubated with 5 μmol·l$^{-1}$ solution of test substance, freshly prepared 2 mmol·l$^{-1}$ solution of NADPH and 2 mmol·l$^{-1}$ MgCl$_2$ in 90 mmol·l$^{-1}$ Tris buffer (pH 7.4). The incubation of 37.5 μl of the mixture was terminated by the addition of 150 μl of acetonitrile containing caffeine as an internal standard, cooled to 0° C. The mixture was vortexed (5 min) and centrifuged (20500 g; 10 min). The supernatant was transferred to a vial, and 1 μl of the mixture was used for LC-MS analysis.

LC-MS Analysis of Samples

Samples were analyzed in a Sciex Qtrap 6550 instrument and a Phenomex column was used for the separation (50× 2.1, 13 nm, 1.7 μm), a flow rate of 0.3 ml/min, and a gradient with a mobile phase fraction of B (0.1% (vol./vol.) formic acid in acetonitrile) continuously increased over 6 minutes from 5 to 100% (vol./vol.) in mobile phase A (0.1% (vol./vol.) formic acid in water). Results are presented as the percentage of test substance versus control (aliquot taken at time 0).

Measurement Results:

Stability was tested for selected inhibitors 3a, 3b, 3e, 5f and 5h.

These substances are stable in human plasma. The highest rate of degradation was observed for substance 5f, where 25% of the substance degraded within 120 minutes. In murine plasma, only substances 3a, 3b and 3e are stable, while substances 5f and 5h degrade immediately (100% of the substance degraded within 20 minutes). In murine microsomes, substances 3a and 3b are stable (a maximum of 20% of the substance degraded within 120 minutes), substances 3e and 5f are partially stable (40-50% of the substance degraded within 120 minutes) and substance 5h is unstable (100% of the substance degraded within 20 minutes).

Example 27

Measurement of Cytotoxicity of α-Ketoamide Inhibitors on Tumour Cell Lines

The cytotoxicity of the substances was measured on four tumour cell lines: CCRF-CEM, HepG2, Hela, HL-60. All cell lines were purchased from ATCC (Manassas, VA, USA). Cells were cultured in RPMI-1640 or DMEM medium containing 10% (wt/wt) FBS and 1% (wt/wt) GlutaMax. Cells were distributed at 2,000-10,000 per well of a 384-well plate (Thermo Fisher Scientific, Waltham, USA) and incubated overnight. After 24 hours, test substance solutions (10 or 100 μmol·l$^{-1}$) were added to the wells and the cells were incubated with the test substances at 37° C. and 5% (vol./vol.) CO$_2$ for another 72 h. XTT dye (XTT cell proliferation kit II, Roche Diagnostics GmbH, Mannheim, Germany) was added to the wells according to the manufacturer's protocol. After one hour of incubation with the dye, the absorbance at 495 nm was measured and the signal was compared with the control (100% viability=cells without test substance).

Results of Cytotoxicity Testing on Human Tumour Cell Lines of Lymphoblastoid Leukaemia, Cervical Cancer, Liver Cancer and Myeloid Leukaemia

| Comp. ID | Cell viability [% vs. control] | | | | | | | |
|---|---|---|---|---|---|---|---|---|
| | CEM | | HL60 | | HeLa S3 | | HepG2 | |
| | 10 μM | 100 μM | 10 μM | 100 μM | 10 μM | 100 μM | 10 μM | 100 μM |
| 3a | 105 | 94 | 94 | 106 | 119 | 96 | 103 | 107 |
| 3b | 106 | 88 | 88 | 100 | 106 | 78 | 97 | 92 |
| 3d | 105 | 85 | 110 | 107 | 86 | 81 | 88 | 89 |
| 3e | 108 | 85 | 101 | 106 | 104 | 86 | 92 | 90 |
| 3f | 92 | 84 | 110 | 108 | 103 | 94 | 95 | 82 |
| 3g | 106 | 73 | 100 | 103 | 98 | 89 | 93 | 63 |
| 3h | 94 | 115 | 110 | 95 | 89 | 103 | 88 | 108 |
| 3i | 93 | 117 | 111 | 100 | 78 | 105 | 87 | 110 |
| 3j | 94 | 119 | 109 | 123 | 93 | 109 | 76 | 124 |
| 3k | 110 | 123 | 112 | 103 | 104 | 94 | 109 | 105 |
| 3l | 104 | 121 | 104 | 111 | 95 | 100 | 97 | 109 |
| 3m | 97 | 120 | 102 | 124 | 108 | 104 | 91 | 105 |
| 5a | 104 | 100 | 105 | 76 | 92 | 102 | 91 | 104 |
| 5b | 90 | 109 | 111 | 86 | 93 | 101 | 83 | 106 |
| 5c | 113 | 108 | 86 | 89 | 119 | 99 | 96 | 108 |
| 5d | 89 | 107 | 112 | 95 | 95 | 96 | 82 | 89 |
| 5e | 96 | 104 | 112 | 83 | 99 | 106 | 75 | 110 |
| 5f | 98 | 72 | 114 | 98 | 96 | 100 | 78 | 121 |
| 5g | 114 | 101 | 88 | 103 | 109 | 99 | 102 | 108 |
| 5h | 114 | 103 | 109 | 106 | 116 | 93 | 112 | 105 |
| 5i | 107 | 107 | 104 | 101 | 94 | 98 | 89 | 101 |

M = mol·l$^{-1}$

INDUSTRIAL APPLICABILITY

The substances disclosed in this application are useful as medicaments for the targeted treatment or diagnostic agents for the targeted diagnosis of tumour growth.

The invention claimed is:

1. Quinolinecarboxamide compounds of general formula I

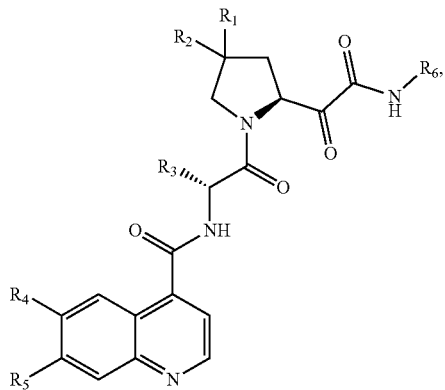

wherein $R_1$ and $R_2$ are independently selected from the group consisting of H, D, and F, $R_3$ is selected from the group consisting of H, D, and C1-C5 alkyl, $R_4$ and $R_5$ are independently selected from the group consisting of H, D, —OH, C1-C3 alkoxy and a structure —X—Y—Z, wherein X is oxygen or —NH—, Y is

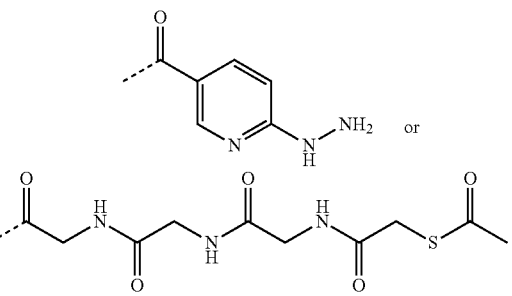

wherein k is an integer from 5 to 15 and m is an integer from 1 to 3, and Z is

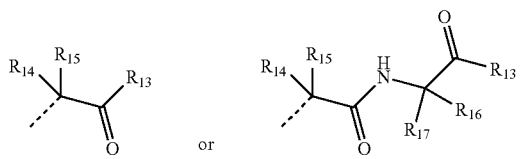

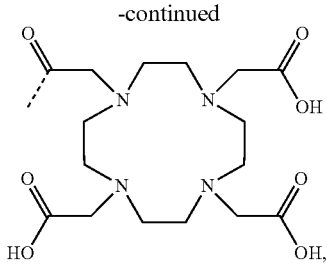

$R_6$ is selected from the group consisting of H, D, C1-C10 alkyl, C3-C10 cycloalkyl, adamantyl, and substituted or unsubstituted aryl or C7-C20 alkylaryl, wherein the aryl is

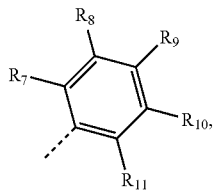

wherein $R_7$ and $R_{11}$ are independently selected from the group consisting of H, D, halogen, C1-C3 alkyl, C1-C3 alkoxy, —CF$_3$, and —C(=O)—OR$_{12}$, wherein $R_{12}$ is selected from the group consisting of H, D, halogen, and C1-C4 alkyl or C1-C2 alkyl, $R_8$, $R_9$ and $R_{10}$ are independently selected from the group consisting of H, D, halogen, —OMe, C1-C3 alkyl, C1-C3 alkoxy or C1-C2 alkoxy, —CF$_3$, and —C(=O)—OR$_{12}$, or $R_6$ is wherein $R_{13}$ is selected from the group consisting of —OR$_{12}$, —NHR$_{12}$, —N(—CH$_3$)R$_{12}$, pyrrolidine, and morpholine, $R_{14}$ and $R_{15}$ are independently selected from the group consisting of H, D, C1-C5 alkyl, phenyl, 3,4-dimethoxyphenyl, benzyl, 3,4-dimethoxybenzyl, and unsubstituted C3-C8 heteroalkylaryl, $R_{16}$ and $R_{17}$ are independently selected from the group consisting of H, D, C1-C6 alkyl, phenyl, benzyl, 4-hydroxybenzyl, unsubstituted C3-C8 heteroalkylaryl, —(CH$_2$)$_n$—C(=O)—OR$_{18}$, —(CH$_2$)$_n$—C(=O)—NR$_{19}$R$_{20}$, and —(CH$_2$)$_n$—NR$_{21}$R$_{22}$, wherein n is an integer from 1 to 4, $R_{18}$ is selected from the group consisting of H, D, C1-C3 alkyl, and benzyl, $R_{19}$ and $R_{20}$ are independently selected from the group consisting of H, D, C1-C3 alkyl, benzyl, and 3,4-dimethoxybenzyl, and $R_{21}$ and $R_{22}$ are independently selected from the group consisting of H, D, and (benzyloxy)carbonyl.

2. Quinolinecarboxamide compounds of the general formula I according to claim 1, selected from the group consisting of (S)—N-(2-(2-(2-(Benzylamino)-2-oxoacetyl)pyrrolidine-1-yl)-2-oxoethyl)quinoline-4-carboxamide,
(S)—N-(2-(2-(2-((3,4-Dimethoxybenzyl)amino)-2-oxoacetyl)pyrrolidine-1-yl)-2-oxoethyl)-quinoline-4-carboxamide,
(S)—N-(2-(2-(2-((4-Fluorobenzyl)amino)-2-oxoacetyl)pyrrolidine-1-yl)-2-oxoethyl)quinoline-4-carboxamide,
(S)—N-(2-Oxo-2-(2-(2-oxo-2-(phenethylamino)acetyl)pyrrolidine-1-yl)ethyl)quinoline-4-carboxamide,
(S)—N-(2-(2-(2-((3,4-Dimethoxyphenethyl)amino)-2-oxoacetyl)pyrrolidine-1-yl)-2-oxoethyl)quinoline-4-carboxamide,
(S)—N-(2-(2-(2-((4-Methoxyphenyl)amino)-2-oxoacetyl)pyrrolidine-1-yl)-2-oxoethyl)quinoline-4-carboxamide,
Methyl(S)-4-(2-oxo-2-(1-((quinoline-4-carbonyl)glycyl)pyrrolidine-2-yl)acetamido)benzoate,
(S)—N-(2-(2-(2-(Cyclopropylamino)-2-oxoacetyl)pyrrolidine-1-yl)-2-oxoethyl)quinoline-4-carboxamide,
(S)—N-(2-(2-(2-(Isopropylamino)-2-oxoacetyl)pyrrolidine-1-yl)-2-oxoethyl)quinoline-4-carboxamide,
(S)—N-(2-Oxo-2-(2-(2-oxo-2-(pentylamino)acetyl)pyrrolidine-1-yl)ethyl)quinoline-4-carboxamide,
Methyl (S)-(2-oxo-2-(1-((quinoline-4-carbonyl)glycyl)pyrrolidine-2-yl)acetyl)glycinate,
tert-Butyl (S)-(2-oxo-2-(1-((quinoline-4-carbonyl)glycyl)pyrrolidine-2-yl)acetyl)glycinate,
Methyl (2-oxo-2-((S)-1-((quinoline-4-carbonyl)glycyl)pyrrolidine-2-yl)acetyl)alaninate,
(S)—N-(2-(2-(2-((2-(Dimethylamino)-2-oxoethyl)amino)-2-oxoacetyl)pyrrolidine-1-yl)-2-oxoethyl)quinoline-4-carboxamide,
(S)—N-(2-(2-(2-((2-(Ethyl(propyl)amino)-2-oxoethyl)amino)-2-oxoacetyl)pyrrolidine-1-yl)-2-oxoethyl)quinoline-4-carboxamide,
(S)—N-(2-(2-(2-((2-(Isopropylamino)-2-oxoethyl)amino)-2-oxoacetyl)pyrrolidine-1-yl)-2-oxoethyl)quinoline-4-carboxamide,
(S)—N-(2-(2-(2-((2-(Benzylamino)-2-oxoethyl)amino)-2-oxoacetyl)pyrrolidine-1-yl)-2-oxoethyl)quinoline-4-carboxamide,
Methyl (2-oxo-2-((S)-1-((quinoline-4-carbonyl)glycyl)pyrrolidine-2-yl)acetyl)glycyl-L-leucinate,
Methyl (2-oxo-2-((S)-1-((quinoline-4-carbonyl)glycyl)pyrrolidine-2-yl)acetyl)glycyl-L-phenylalaninate,
Methyl (2-oxo-2-((S)-1-((quinoline-4-carbonyl)glycyl)pyrrolidine-2-yl)acetyl)glycyl-L-glutaminate, 5-Benzyl 1-methyl (2-oxo-2-((S)-1-((quinoline-4-carbonyl)glycyl)pyrrolidine-2-yl)acetyl)-glycyl-L-glutamate,
Benzyl N$^6$-((benzyloxy)carbonyl)-N$^2$-((2-oxo-2-((S)-1-((quinoline-4-carbonyl)glycyl)-pyrrolidine-2-yl)acetyl)glycyl)-L-lysinate,
(S)—S-(62-((4-((2-(2-(2-((3,4-dimethoxybenzyl)amino)-2-oxoacetyl)pyrrolidine-1-yl)-2-oxoethyl)carbamoyl)quinoline-7-yl)oxy)-2,5,8,11,61-pentaoxo-15,18,21,24,27,30,33,36,39,42,45,48,51,54,57-pentadecaoxa-3,6,9,12,60-pentaaza-dohexacontyl)-ethanethioate, and
(S)—N-(2-(2-(2-((3,4-dimethoxybenzyl)amino)-2-oxoacetyl)pyrrolidine-1-yl)-2-oxoethyl)-7-(2-(6-hydrazinylnicotinamido)ethoxy)quinoline-4-carboxamide.

3. A method of administering a medicament, comprising the step of administering guinolinecarboxamide compounds of the general formula I according to claim 1 to a subject in need thereof.

4. A method of administering a medicament, comprising the step of administering guinolinecarboxamide compounds of the general formula I according to claim 1 in treatment of cancer to a subject in need thereof.

5. A method of administering a medicament, comprising the step of administering guinolinecarboxamide compounds of the general formula I according to claim 1 in treatment of epithelial tumours to a subject in need thereof.

6. A method of administering a diagnostic composition comprising the step of administering quinolinecarboxamide compounds of the general formula I according to claim 1 in targeted diagnostics of tumour tissue.

7. A method of administering a diagnostic composition comprising the step of administering guinolinecarboxamide compounds of the general formula I according to claim 1 in targeted diagnostics of epithelial tumours.

8. A pharmaceutical composition comprising a therapeutically effective amount of a compound of the general formula I according to claim 1 and optionally at least one pharmaceutically acceptable carrier, excipient and/or diluent.

9. A method of treating epithelia tumours comprising administering an effective amount of the composition according to claim 8 in the treatment of cancer.

10. A diagnostic composition comprising a therapeutically effective amount of a compound of the general formula I according to claim 1 and optionally at least one pharmaceutically acceptable carrier, filler and/or diluent.

11. The diagnostic composition comprising a therapeutically effective amount of a compound of the general formula I according to claim 10 in targeted diagnostics of tumour tissue.

12. The diagnostic composition comprising a therapeutically effective amount of a compound of the general formula I according to claim 10 in targeted diagnostics of epithelial tumours.

* * * * *